United States Patent [19]

König et al.

[11] Patent Number: 5,091,367

[45] Date of Patent: Feb. 25, 1992

[54] ANALOGS OF GONADOLIBERIN WITH IMPROVED SOLUBILITY, METHODS FOR THEIR PREPARATION, AGENTS CONTAINING THEM AND THEIR USE

[75] Inventors: Wolfgang König, Hofheim am Taunus; Jürgen K. Sandow, Königstein/Taunus; Cenek Kolar, Marburg, all of Fed. Rep. of Germany

[73] Assignee: Hoechst Aktiengesellschaft, Frankfurt am Main, Fed. Rep. of Germany

[21] Appl. No.: 724,477

[22] Filed: Jun. 28, 1991

Related U.S. Application Data

[63] Continuation of Ser. No. 390,477, Aug. 7, 1989, abandoned, which is a continuation of Ser. No. 105,240, Oct. 7, 1987, abandoned.

[30] Foreign Application Priority Data

Oct. 9, 1986 [DE] Fed. Rep. of Germany ....... 3634435

[51] Int. Cl.$^5$ .................... A61K 37/02; A61K 37/43; C07K 7/06; C07K 7/20
[52] U.S. Cl. .................................. 514/15; 530/313; 530/328; 514/800
[58] Field of Search ................. 530/313, 328; 514/15, 514/800

[56] References Cited

U.S. PATENT DOCUMENTS 4,472,382 9/1984 Labrie et al. ............................ 514/15
4,728,640 3/1988 Labrie et al. ............................ 514/15

FOREIGN PATENT DOCUMENTS 2465486 3/1981 France .
188987 2/1982 New Zealand .
200125 10/1984 New Zealand .
204692 3/1986 New Zealand .

OTHER PUBLICATIONS

Chem. Abstr., vol. 110, 58099v (1989).
Synthesis of a Glycotripeptide and a Glycosomatostatin Containing the 3-O-(2-Acetamido-2-Deoxy-β-D--Glucopyranosyl)-L-Serine Residue.

*Primary Examiner*—Lester L. Lee
*Attorney, Agent, or Firm*—Finnegan, Henderson, Farabow, Garrett, and Dunner

[57] ABSTRACT

The invention relates to peptides of the formula

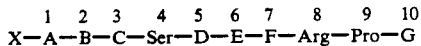

in which X is absent or is hydrogen or acyl; A is Pgl, de-hydro-Pro, Pro, D-Thi or D-Pgl or represents optionally substituted D-Nal(2), D-Phe or D-Trp; B is His or optionally substituted D-Phe; C is Trp, D-Thi, D-Pal(3) or optionally substituted D-Trp; D is Tyr, Arg of His; E is D-Ser(R$^1$), β-Asn, β-Asp-OMe, D-Thi or —NH—CH(CH$_2$R$^2$)—CO—; F is Ser(R$^1$), Leu, Trp or Phe; G is Gly-NH$_2$, Aza-Gly-NH$_2$, D-Ala-NH$_2$ or NH-alkyl; R$^1$ is glycosyl and R$^2$ is hydrogen, acyl, aryl or heteroaryl.

The invention also relates to methods for the preparation of these peptides, agents containing them and their use.

11 Claims, No Drawings

ANALOGS OF GONADOLIBERIN WITH IMPROVED SOLUBILITY, METHODS FOR THEIR PREPARATION, AGENTS CONTAINING THEM AND THEIR USE

This application is a continuation of application Ser. No. 390,477, filed Aug. 7, 1989, now abandoned, which is a continuation of application Ser. No. 105,240, filed Oct. 7, 1987, now abandoned.

Naturally occurring gonadoliberins (Gn-RH) from various species are decapeptides of the following structure:

| | |
|---|---|
| h-,p-,o-Gn—RH | Pgl—His—Trp—Ser—Tyr—Gly—Leu—Arg—Pro—Gly—NH$_2$ |
| g-Gn—RH—I | Pgl—His—Trp—Ser—Tyr—Gly—Leu—Gln—Pro—Gly—NH$_2$ |
| g-Gn—RH—II | Pgl—His—Trp—Ser—His—Gly—Trp—Tyr—Pro—Gly—NH$_2$ |
| sa-Gn—RH | Pgl—His—Trp—Ser—Tyr—Gly Trp—Leu—Pro—Gly—NH$_2$ |
| pe-Gn—RH | Pgl—His—Tyr—Ser—Leu—Glu—Trp—Lys—Pro—Gly—NH$_2$ |

[h- (human), p- (pig), o- (sheep): Biochem. Biophys. Res. Commun. 43 (1971) 1334; g- (chicken-I): South Africa J. Science 78 (1982) 124; g- (chicken-II): Proc. Natl. Acad. Sci. USA 81 (1984) 3874; sa- (salmon): Proc. Natl. Acad. Sci. USA 80 (1983) 2794; pe- (lamprey): J. Biol. Chem. 261 (1986) 48124819.]

Gn-RH is formed in mammals chiefly in the hypothalamus and causes a secretion of lutropin (LH) and follitropin (FSH) in the hypophysis.

When glycine in position 6 is replaced by hydrophobic D-amino acids and/or glycinamide in position 10 is replaced by ethylamine, highly active Gn-RH agonists are obtained [M. J. Karten and J. E. Rivier, Endocrine Reviews 7 (1986) 44–66]. As a result of these substitutions, the Gn-RH-agonists become less soluble in aqueous solutions. In the Gn-RH-antagonists, in which the hydrophilic positions 1, 2 and 10 are also exchanged for hydrophobic amino acids, the solubility in water decreased even further. Good water solubility is necessary above all for parenteral and intranasal use: the active compound can be administered in a smaller volume. By introduction of a basic D-amino acid (D-Arg, D-Lys, DHar(Et)$_2$) in position 6, the solubility in the Gn-RH-antagonists was raised, however these derivatives are not well tolerated, as through the introduction of a second positive charge into the molecule they cause histamine secretion and mediator release.

It has been found that by introduction of D-serine O-glycosides in position 6 and/or L-serine O-glycosides in position 7 the water solubility of Gn-RH-analogs could be considerably improved, whereas their biological activity unexpectedly remained very good.

The invention relates to peptides of the general formula I,

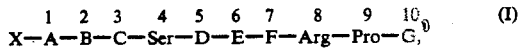

(I)

in which

X is hydrogen or (C$_1$–C$_7$)-acyl or, if A represents pyroglutamyl, is absent;

A is Pgl, dehydro-Pro, Pro, D-Thi, D-Pgl or D-Nal(2) optionally substituted in the aromatic ring by one or two identical or different radicals from the series bromo, chloro, fluoro, nitro, amino, methyl and methoxy, D-Phe substituted in this way or D-Trp substituted in this way;

B is His or D-Phe optionally substituted in the phenyl ring by one or two identical or different radicals from the series bromo, chloro, fluoro, nitro, amino, methyl and methoxy;

C is Trp, D-Thi, D-Pal(3) or D-Trp optionally substituted in position 5 and/or 6 by one or two identical or different radicals from the series bromo, chloro, fluoro, nitro, amino, methyl or methoxy;

D is Tyr, Arg, or His;

E is D-Ser(R$^1$), β-Asn, β-Asp-OMe, D-Thi or the radical of a D-amino acid of the general formula II;

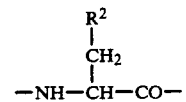

(II)

F is Ser(R$^1$), Leu, Trp or Phe;

G is Gly-NH$_2$, Aza-Gly-NH$_2$, D-Ala-NH$_2$ or NH-(C$_1$–C$_4$)-alkyl, preferably NH-C$_2$H$_5$;

R$^1$ is an optionally partly protected glycosyl residue with at least one free hydroxyl group and R$^2$ is hydrogen, (C$_1$–C$_4$)-alkoxycarbonyl, (C$_1$–C$_4$)-alkoxy, (C$_1$–C$_4$)-alkyl, which is optionally monosubstituted by (C$_1$–C$_4$)-alkoxycarbonyl or (C$_1$–C$_4$)alkoxycarbonylamino, phenyl, which is optionally substituted by up to three identical or different radicals from the series chloro, fluoro, methyl and (C$_1$–C$_4$)-alkoxy, naphthyl, 4,5,6,7-tetrahydrobenzimidazol-2-yl or indolyl, and to their physiologically acceptable salts, with the proviso that a) if E represents a radical of the formula II, β-Asn, β-Asp-OMe or D-Thi, F is exclusively Ser(R$^1$) and b) if F represents Leu, Phe or Trp, E is exclusively D-Ser(R$^1$)

X as (C$_1$–C$_7$)-acyl preferably represents (C$_1$–C$_7$)-alkanoyl, especially acetyl, or benzoyl or (C$_1$–C$_6$)alkoxycarbonyl.

Alkyl residues can be straight-chain or branched.

Unless otherwise stated, the three-letter symbols (see e.g. Pure Appl. Chem. 56 [1984]595–624, and Eur. J. Biochem. 138 [1984]9–37) are used in formula I and below for the amino acid radicals. These symbols are preceded by the symbol "D", when it corresponds to the radicals of a D-amino acid; radicals without configuration symbols are L-configured.

Protective groups are abbreviated by the methods used in the literature (see e.g. Wunsch et al., Synthese von Peptiden [Synthesis of Peptides](Houben-Weyl 15/1,2), Stuttgart, Thieme 1974).

Gn-RH-Agonists of general formula I are preferred, in which

X is absent;
A is Pgl;
B is His;
C is Trp;
D is Tyr or His;
E is D-Ser(R$^1$), β-Asn, β-Asp-OMe or the radical of a D-amino acid of the formula II;
F is Ser(R$^1$), Trp or Leu and G is Gly-NH$_2$, Aza-Gly-NH$_2$ or NH-(C$_1$-C$_4$)-alkyl, preferably -NH-C$_2$H$_5$, and R$^1$ and R$^2$ are as defined above, as well as Gn-RH-antagonists of general formula I, in which X is hydrogen or (C$_1$-C$_7$)-acyl or is absent;

A is dehydro-Pro, Pro, D-Thi, D-Pgl, optionally substituted D-Nal(2), optionally substituted D-Phe or optionally substituted D-Trp;

B is optionally substituted D-Phe;

C is optionally substituted D-Trp, D-Thi or D-Pal(3);

D is Tyr, Arg, or His;

E is D-Ser(R$^1$), D-Thi, or the radical of a D-amino acid of the formula II;

F is Ser(R$^1$), Leu, Phe or Trp and

G is Gly-NH$_2$, D-Ala-NH$_2$, Aza-Gly-NH$_2$ or NH-(C$_1$-C$_4$)-alkyl, preferably NH-C$_2$H$_5$, and R$^1$ and R$^2$ are as defined above.

Particularly preferred antagonists are those where

X is (C$_1$-C$_7$)-acyl, preferably acetyl;

A is D-Nal(2);

B is D-Phe(Cl);

C is D-Trp;

D is Tyr, His or Arg;

E is D-Ser(R$^1$);

F is Ser(R$^1$), Leu, Phe or Trp and

G is D-Ala-NH$_2$ or Aza-Gly-NH$_2$.

R$^1$ is preferably a glycosyl residue partly protected with one of the protecting groups usual in carbohydrate chemistry or an unprotected glycosyl radical, which is derived from a glycopyranose, glycofuranose or an oligosaccharide. At least one hydroxyl group should be unprotected.

Gn-RH-Analogs with unprotected glycosyl radicals are particularly preferred. The glycosyl radical can be connected both α- and β-glycosidically to the serine radical.

R$^1$ can be a glucofuranosyl or glucopyranosyl radical for example, which is derived from naturally occurring aldotetroses, aldopentoses, aldohexoses, ketopentoses, ketohexoses, deoxyaldoses, aminoaldoses and oligosaccharides, such as di- and tri-saccharides, as well as their stereoisomers.

These glycosyl radicals in particular are derived from D- or L-monosaccharides which occur naturally in microorganisms, plants, animals or humans, such as ribose (Rib), arabinose (Ara), xylose (Xyl), lyxose (Lyx), allose (All), altrose (Alt), glucose (Glc), mannose (Man), gulose (Gul), idose (Ido), galactose (Gal), talose (Tal), erythrose (Ery), threose (Thr), psicose (Psi), fructose (Fru), sorbose (Sor), tagatose (Tag), xylulose (Xyu), fucose (Fuc), rhamnose (Rha), olivose (Oli), oliose (Olo), mycarose (Myc), rhodosamine (RN), N-acetylglucosamine (GlcNAc), N-acetylgalactosamine (GalNAc), N-acetylmannosamine (ManNAc), or disaccharides, such as maltose (Mal), lactose (Lac), cellobiose (Cel), gentibiose (Gen), N-acetyllactosamine (LacNAc), chitobiose (Chit), β-galactopyranosyl-(1-3)-N-acetylgalactosamine and β-galactopyranosyl-(1-3)- or -(1-4)-N-acetylglucosamine, as well as their synthetic derivatives, such as 2-deoxy-, 2-amino-, 2-acetamido- or 2-halogeno-, preferably bromo- and iodo-sugars.

By the term protecting groups usual in carbohydrate chemistry are understood e.g. the (C$_1$-C$_{10}$)-acyl protective groups such as (C$_1$-C$_6$)-alkanoyl (e.g. acetyl, trichloroacetyl, trifluoroacetyl), benzoyl or para-nitrobenzyl, as well as optionally modified methyl, methoxymethyl, benzyl, tetrahydropyranyl, benzylidene, isopropylidene or trityl groups, of which the acyl protective groups, especially the acetyl (Ac) group are particularly preferred.

By physiologically acceptable salts are understood in particular those with inorganic acids, such as HCl, HBr, H$_2$SO$_4$, H$_3$PO$_4$, or organic acids, such as acetic acid, maleic acid, fumaric acid, tartaric acid and citric acid.

The invention also relates to a method for the preparation of peptides of the general formula I, wherein a fragment with a free N-terminal amino group is condensed with a fragment with a free C-terminal carboxyl group, one or more protective groups optionally introduced temporarily for the protection of functional groups are removed and the peptide thus obtained is optionally converted into its physiologically acceptable salt.

The choice of the protective groups and the synthesis strategy are determined by the type and configuration of the amino acids as well as by type of coupling conditions.

The condensation according to the method of the invention takes place according to the general methods of peptide chemistry, preferably according to the mixed anhydride method, via active esters, azides or according to the carbodiimide methods, in particular with the addition of substances which accelerate the reaction and prevent racemization such as e.g. 1-hydroxybenzotriazole, N-hydroxysuccinimide, 3-hydroxy-4-oxo-3,4-dihydro-1,2,3-benzotriazine, N-hydroxy-5-norbornene-2,3-dicarboximide, and in addition with the use of activated derivatives of 1-hydroxybenzotriazole or anhydrides of phosphoric, phosphonic and phosphinic acids at a reaction temperature between −10° C. and the boiling point of the reaction mixture, preferably between −5° C. and 40° C.

Suitable solvents are dimethylformamide, dimethylacetamide, phosphoric acid hexamethyltriamide, N-methylpyrrolidone or dimethylsulfoxide. Inasmuch as the solubility of the components permits, solvents such as methylene chloride or chloroform can also be employed. The methods mentioned are described e.g. in Meienhofer-Gross: "The Peptides", Academic Press, volume I (1979).

For the introduction of the glycosyl radicals into L- or D-serine, the amino group and the carboxyl group must first be suitably protected. Particularly convenient protective groups have proved to be those which can be removed by catalytic hydrogenation or by secondary amines. In the former case these protective groups are of the benzyl type, such as e.g. the benzyloxycarbonyl (Z-) or p-nitrobenzyloxycarbonyl radicals as amino-protecting groups and the benzyl (-OBzl) or p-nitrobenzyl esters for the carboxyl group. With secondary amines the 9-fluorenylmethyloxycarbonyl (Fmoc-) radical can be removed. The use of Fmoc-L- or Fmoc-D-Ser-OBzl, in the case of which the benzylesters of the corresponding Fmoc-L- or Fmoc-D-Ser(R$^1$)-OBzl can be selectively removed by catalytic hydrogenation after glycosylation has proved to be particularly convenient. This is particularly surprising, since it was recently reported repeatedly that the Fmoc radical is removed by catalytic hydrogenation [e.g. by R. Geiger and W. König in E. Gross and J. Meienhofer (eds): The Peptides, volume 3, page 24, Academic Press, 1981].

In the synthesis of the O-glycosylserine units two polyfunctional reactants have to be joined (carbohydrate and serine). Both must allow selective blocking and unblocking. The anomeric center in the glycosyl component must be available and functionalizable and only the hydroxyl group necessary for coupling may be unblocked in the serine component. According to the type of desired glycosidic bonds (1,2-cis- or 1,2-trans-glycoside) it is necessary to establish suitable protective groups for the blocking of the hydroxy or amino groups in the glycosyl components as well as to select reaction conditions for the coupling step which leads stereoselectively to only one of the two possible anomers.

For the preparation of the Gn-RH analogs according to the invention, both the glycosyl-serine units known from the literature, most of which are natural, e.g. such as are described by K. Dill et al. [Carbohydr. Res. 123 (1983) 137–144], H. Kunz [Nach. Chem. Tech. Lab. 32 (1984) 11]and H. Paulsen [Chem. Soc. Res. 13 (1) (1984) 25–45], and the artificial glycosyl-serine derivatives, which are obtained by the described or modified glycosylation methods usual in carbohydrate chemistry, e.g. those according to A. F. Bochkov and G. E. Zaikov [Chemistry of the 0-glycosidic bond, Pergamon Press 157 (1979)], H. Paulsen [Angew. Chem. 94 (1982) 184–201]and R. R. Schmidt [Angew. Chem. 98 (1986) 213–236], are used.

The peptides according to the invention can be prepared using the general peptide chemistry methods (Houben-Weyl, Methoden der Organischen Chemie [Methods in organic chemistry], volume 15/1,2), for example stepwise from the C terminal end or by coupling of fragments. For the Gn-RH agonists the coupling of fragments according to the scheme

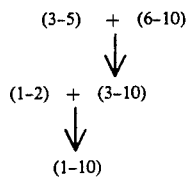

is particularly preferred.

In order to minimize racemization in the coupling of the fragments, it is preferred here to use dicyclohexylcarbodiimide (DCC) with the addition of 3-hydroxy-4-oxo-3,4-dihydro-1,2,3-benzotriazine (HOObt). The Z-radical cleavable by catalytic hydrogenation or the Fmoc-radical cleavable by secondary amines are preferably employed as aminoprotecting groups. The imidazole ring of the histidine is preferably protected by the 2,4-dinitrophenyl (Dnp) radical, which can be cleaved by mercaptans or hydrazine.

The antagonists according to the invention can likewise be prepared from the C-terminal end. However, coupling of fragments is more economical here, as e.g.

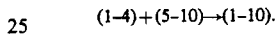

When acyl groups are used as the protective groups for the hydroxyl groups of the glycoside radical and hydrazine is used for cleaving the protective groups, almost fully deprotected peptides as well as peptide derivatives, in which the Dnp radical is completely cleaved 1–2 acyl groups still remain in the glycosyl radical, can be isolated.

Table 1 shows the solubility of the synthesized peptides and glycopeptides in a well compatible neutral buffer, is used for the nasal application of protirelin such as [Horm. Metab. Res. 15 (1983) 52], and the biological activity in rat super-ovulation.

TABLE 1

| | $ED_{20-50}$ Super-ovul. (ng/rat) | Solubility in neutral nasal buffer (mg/ml) |
|---|---|---|
| Pgl—His—Trp—Ser—Tyr—D-Ser(tBu)—Leu—Arg—Pro—NH—$C_2H_5$ (= Buserelin) | 3 | 1.25 |
| Pgl—His—Trp—Ser—Tyr—D-Ser($\beta$-D-Glc)—Leu—Arg—Pro—NH—$C_2H_5$ | 12 | 125.0 |
| Pgl—His—Trp—Ser—Tyr—D-Ser($\alpha$-D-Man)—Leu—Arg—Pro—NH—$C_2H_5$ | 6 | 62.5 |
| Pgl—His—Trp—Ser—Tyr—D-Ser ($\beta$-L-Fuc)—Leu—Arg—Pro—NH—$C_2H_5$ | 6 | 167.0 |
| Pgl—His—Trp—Ser—Tyr—D-Ser(Ac—$\beta$-L-Fuc)—Leu—Arg—Pro—NH—$C_2H_5$ | 6 | 10.0 |
| Pgl—His—Trp—Ser—Tyr—D-Ser($\beta$-D-Xyl)—Leu—Arg—Pro—NH—$C_2H_5$ | 6 | 50.0 |
| Pgl—His—Trp—Ser—Tyr—D-Ser($\alpha$-L-Rha)—Leu—Arg—Pro—NH—$C_2H_5$ | 3 | 167.0 |
| Pgl—His—Trp—Ser—Tyr—D-Ser(Ac—$\alpha$-L-Rha)—Leu—Arg—Pro—NH—$C_2H_5$ | 3 | 50.0 |
| Pgl—His—Trp—Ser—Tyr—D-Trp—Leu—Arg—Pro—NH—$C_2H_5$ (LH—RH—T) | 3 | 0.33 |
| Pgl—His—Trp—Ser—Tyr—D-Trp—Ser($\beta$-D-Glc)—Arg—Pro—NH—$C_2H_5$ | 6 | 2.5 |
| Pgl—His—Trp—Ser—Tyr—D-Trp—Ser(Ac—$\beta$-D-Glc)—Arg—Pro—NH—$C_2H_5$ | 5 | 2.5 |
| Pgl—His—Trp—Ser—Tyr—D-Trp—Ser($\beta$-L-Fuc)—Arg—Pro—NH—$C_2H_5$ | >200 | 2.5 |
| Pgl—His—Trp—Ser—Tyr—D-Trp—Ser(Ac—$\beta$-L-Fuc)—Arg—Pro—NH—$C_2H_5$ | 200 | 10.0 |
| Pgl—His—Trp—Ser—Tyr—D-Trp—Ser($Ac_2$—$\beta$-L-Fuc)—Arg—Pro—NH—$C_2H_5$ | 200 | 3.3 |
| Pgl—His—Trp—Ser—Tyr—D-Trp—Ser($\alpha$-D-Man)—Arg—Pro—NH—$C_2H_5$ | >24 | 3.3 |
| Pgl—His—Trp—Ser—Tyr—D-Trp—Ser(Ac—$\alpha$-D- | >24 | 10.0 |

TABLE 1-continued

| | ED$_{20-50}$ Super-ovul. (ng/rat) | Solubility in neutral nasal buffer (mg/ml) |
|---|---|---|
| Pgl—His—Trp—Ser—Tyr—D-Trp—Ser(Ac$_2$—α-D-Man)—Arg—Pro—NH—C$_2$H$_5$ | >24 | 10.0 |
| Pgl—His—Trp—Ser—Tyr—D-Trp—Ser(β-D-Xyl)—Arg—Pro—NH—C$_2$H$_5$ | 6 | 1.7 |
| Pgl—His—Trp—Ser—Tyr—D-Trp—Ser(Ac—β-D-Xyl)—Arg—Pro—NH—C$_2$H$_5$ | 6 | 2.5 |
| Pgl—His—Trp—Ser—Tyr—D-Trp—Ser(α-L-Rha)—Arg—Pro—NH—C$_2$H$_5$ | >24 | 1.4 |
| Pgl—His—Trp—Ser—Tyr—D-Trp—Ser(Ac—α-L-Rha)—Arg—Pro—NH—C$_2$H$_5$ | >24 | 0.5 |
| Pgl—His—Trp—Ser—Tyr—D-Ser(β-L-Xyl)—Leu—Arg—Pro—NH—C$_2$H$_5$ | 6 | 10 |
| Pgl—His—Trp—Ser—Tyr—D-Ser(β-Lac)—Leu—Arg—Pro—NH—C$_2$H$_5$ | 12 | 167 |
| Pgl—His—Trp—Ser—Tyr—D-Ser(β-D-Gal)—Leu—Arg—Pro—NH—C$_2$H$_5$ | 12 | 125 |
| Pgl—His—Trp—Ser—Tyr—D-Ser(α-L-Ara)—Leu—Arg—Pro—NH—C$_2$H$_5$ | 12 | 125 |
| Pgl—His—Trp—Ser—Tyr—D-Ser(α-D-Ara)—Leu—Arg—Pro—NH—C$_2$H$_5$ | <24 | 125 |
| Pgl—His—Trp—Ser—Tyr—D-Ser(β-D-Rib)—Leu—Arg—Pro—NH—C$_2$H$_5$ | <6 | 10 |
| Pgl—His—Trp—Ser—Tyr—D-Ser(β-D-GlcNAc)—Leu—Arg—Pro—NH—C$_2$H$_5$ | <6 | 125 |
| Pgl—His—Trp—Ser—Tyr—D-Trp—Ser(β-L-Xyl)—Arg—Pro—NH—C$_2$H$_5$ | 48 | 1.1 |
| Pgl—His—Trp—Ser—Tyr—D-Trp—Ser(β-Lac)—Arg—Pro—NH—C$_2$H$_5$ | <48 | 167 |
| Pgl—His—Trp—Ser—Tyr—D-Trp—Ser(β-D-Gal)—Arg—Pro—NH—C$_2$H$_5$ | n.d. | 10 |
| Pgl—His—Trp—Ser—Tyr—D-Trp—Ser(α-L-Ara)—Arg—Pro—NH—C$_2$H$_5$ | 48 | 1.25 |
| Pgl—His—Trp—Ser—Tyr—D-Trp—Ser(α-D-Ara)—Arg—Pro—NH—C$_2$H$_5$ | 24 | 5 |
| Pgl—His—Trp—Ser—Tyr—D-Trp—Ser(β-L-Rib)—Arg—Pro—NH—C$_2$H$_5$ | <24 | 25 |
| Pgl—His—Trp—Ser—Tyr—D-Trp—Ser(β-D-GlcNAc)—Arg—Pro—NH—C$_2$H$_5$ | >24 | 125 |

Table 1 shows that all the peptides with incorporated D-Ser(R$^1$) or Ser(R$^1$) are more soluble than the corresponding reference substance buserelin or LH-RH-T. The biological activity is very well maintained on the substitution of D-Ser(R$^1$) in position 6, so that the ratio of solubility to biological activity in all compounds according to the invention is higher than that of buserelin. It is, however, also dependent on the type of sugar in position 7.

The Gn-RH agonists according to the invention already have a fertility-increasing action in low doses through secretion of gonadotropin and in repeated high daily doses a contraceptive action by inhibition of the secretion of gonadotropin. Indications are e.g. primary, but predominantly secondary amenorrhea or Corpus luteum insufficiency in women at low doses, and oligospermia in men. Late puberty of both sexes and cryptorchism in children can be treated in addition. In high doses the compounds have an inhibiting action on the formation of both gonadotropin and of testosterone and estrogen and can therefore be used in steroid-dependent diseases, such as e.g. in prostate or breast cancer, in endometriosis or in premature commencement of puberty.

Doses of the compounds according to the invention, which lie still beneath the threshold dose for gonadotropin release, regulate the plasma parathormone (PTH) level. This means that a high PTH level is reduced and low PTH level increased. Probably via this PTH-regulating action, the blood sugar is also influenced, since PTH stimulates glucagon, which in turn raises blood glucose. If the plasma PTH is lowered (e.g. by glucose) then the glycopeptides raise blood glucose. At raised plasma PTH levels, however, the glycopeptide according to the invention should lower blood sugar. Thus it is known that in hyperparathyroidism (raised plasma PTH level) the glucose metabolism and the insulin sensitivity are reduced [J. Clin. Endocrinol. Metab. 60 (1985) 229]. The glycopeptides according to the invention could also be responsible e.g. for lowering plasma PTH and blood glucose in hyperparathryroidism. Raised plasma PTH is also found in patients with liver diseases [Clin. Endocr. 19 (1983) 21-28; Acta Endocrinologica 111 (1986) 62-68]and Osteoporosis [Horm. metab. Res. 17 (1985) 370-373]. Since these compounds stimulate the gonads to steroid hormone synthesis in doses already below the threshold dose for gonadotropin secretion [Biochem. J. 232 (1985) 55-59], they can also be used in very low doses in estrogen or testosterone under-function. During and after puberty, as well as before and after the menopause, the glycopeptides according to the invention can be employed for the stimulation of testosterone and estrogen synthesis. Both estrogen and testosterone are of great importance in bone formation [Clin. Endocrinol. Metab. 9 (1980) 177-205; Acta Endocrinologica 107 (1984) 428-432]. Therefore in addition to pre- and post-menopausal complaints, bone pains and osteoporosis, which also depend on low estrogen or testosterone levels can be treated with the peptides according to the invention. Since PTH itself lowers blood pressure [Hypertension 5 (1983) Suppl. I, 59–63], the blood pressure can also be raised or lowered by raising or lowering the PTH level with the substances according to the invention. In hyperparathyroidism the blood pressure is remarkably raised in about 40% of the cases in spite of the raised PTH [Adv. Exp. Med. Biol. 151 (1982) 619]. This is due to the high calcium level, since PTH boosts the hypertensive effect of a hypercalcemia [Am. J. Physiol. 250 (1986) F924–F926]. Thus the glycopeptides according to the invention also have a blood pressure-lowering effect in hypertensive hyperparathyroidism.

The Gn-RH antagonists according to the invention have an inhibitory effect on the formation of lutropin and follitropin and, as a result, also on the synthesis of testosterone and estrogen (see Table 2). They can be employed as high-dose Gn-RH agonists in gonadotropin- and steroid-dependent diseases.

|  | Serum testosterone (ng/ml) |
|---|---|
| untreated control | 3.63 ± 0.59 |
| Ac—D-Nal—p—Cl—D-Phe—D-Trp—Ser—His—D-Ser($\alpha$-L-Rha)—Leu—Arg—Pro—Azagly—NH$_2$ | 1.34 ± 0.17 |
| Ac—D-Nal—p—Cl—D-Phe—D-Trp—Ser—Tyr—D-Ser($\alpha$-L-Rha)—Leu—Arg—Pro—Azagly—NH$_2$ | 2.30 ± 0.47 |
| Ac—D-Nal—p—Cl—D-Phe—D-Trp—Ser—Arg—D-Ser($\alpha$-L-Rha)—Leu—Arg—Pro—Azagly—NH$_2$ | 2.27 ± 0.28 |

The compounds according to the invention can be administered intranasally or parenterally in corresponding pharmaceutical formulations. For a nasal preparation the compounds are mixed with the usual additives such as stabilizers or inert diluents and converted by the usual methods into suitable forms for administration, such as aqueous, alcoholic or oily suspensions or aqueous, alcoholic or oily solutions. Chelating agents, ethylenediamine-N,N,N',N'tetraacetic acid, citric acid, tartaric acid or their salts can be added to aqueous intranasal preparations. Vegetable or animal oils, such as sunflower oil or cod liver oil, can be used as oily carriers or solvents.

For subcutaneous or intravenous application, the active substances or their physiologically acceptable salts are brought, if desired with the usual substances such as solubilizers, emulsifiers or further auxiliaries, into solution, suspension or emulsion.

As solvents for the new active compounds and the corresponding physiologically acceptable salts can be considered: e.g. water, physiological salt solutions or alcohols, e.g. ethanol, propanediol or glycerol, and also sugar solutions such as glucose or mannitol solutions, or also a mixture of the different solvents mentioned.

The preferred forms for application in humans are intranasal application or the use of implants, since the absorption from the gastrointestinal tract is only slight, and if a daily parenteral administration appears unsuitable for the patients.

About 0.02–0.2 ml of a buffer solution, in which the necessary amount of active compound is dissolved, is sprayed into the nose through a nozzle by means of a dose atomizer. For a single stimulation of gonadotropins, the Gn-RH agonist is applied in general in a nasal daily dose of 25 to 100 μg/patient. In cryptorchism, about 5–25 ug/day and patient are sufficient (administered as nasal solution). On account of the long duration of action of Gn-RH agonists, they can be applied at longer intervals (1–3 days) for the stimulation of the gonadotropins. For inhibiting the gonadotropins and thus adjusting the estrogen and testosterone synthesis, daily higher doses of the Gn-RH agonists must be administered. About 200 to 500 μg are needed several times daily per patient by nasal administration. For the regulation of the plasma PTH level and the direct stimulation of the gonads, about 2.5 to 10 μg/day and patient are needed. On parenteral administration the doses in comparison with the intranasal dose can be reduced by about a power of ten.

The single dose in implants for steroid suppression in humans amounts to 3 to 8 mg of a Gn-RH agonist for a period of 4 to 8 weeks (dose interval) each time. Copolymers of lactic acid and glycollic acid, as well as poly-(3-hydroxybutyric acid) are used preferably as carriers for the implant. The preceding and following doses in humans are based, excepting for cryptorchism, on a normal adult body weight of about 75 kg.

In veterinary medicine, the Gn-RH agonists according to the invention are preferably used parenterally. The Gn-RH agonists can be employed for the treatment of acyclic animals and for ovulation induction and synchronization. The dose varies according to the species of animal. A dose of e.g. 10–20 μg in the cow, 20–40 μg in the mare and 0.5–1 μg in the rabbit is recommended. A stimulation of gonad function can be achieved in the cow by using a single dose implant of 3–300 μg for a period of 2–4 weeks.

The antagonists according to the invention were administered intranasally in doses of 1–10 mg to adult humans. The single dose in implants amounts to about 5–50 mg for a period of 4–8 weeks each. Parenterally administered, 0.1–1 mg is sufficient.

Other abbreviations used:

| HOBt | 1-hydroxybenzotriazole |
|---|---|
| Nal(2) | 2-naphthylalanine |
| —ONSu | N-hydroxysuccinimide ester |
| Pal(3) | 3-pyridinylalanine |
| Pgl | pyroglutamic acid |
| Phe(Cl) | p-chlorophenylalanine |
| Thi | 2-thienylalanine |
| Har | homoarginine |

The examples which follow serve to illustrate the present invention, without limiting it.

Examples

EXAMPLE 1

Pgl-His-Trp-Ser-Tyr-D-Ser($\beta$-D-Glc)-Leu-Arg-Pro-NH-C$_2$H$_5$

1a. Z-D-Ser(Ac$_4$-$\beta$-D-Glc)-OBzl 8.3 g of Z-D-Ser-OBzl (24.17 mmol) are dissolved in a mixture of 80 ml of toluene and 80 ml of nitromethane. After addition of 5.16 g (20.24 mmol) of Hg(CN)$_2$ the reaction mixture is heated to 60° C. and then treated in portions with 13.0 g (31.42 mmol) of 2,3,4,6-tetra-O-acetyl-$\alpha$-D-glucopyranosyl bromide. After a reaction time of 3 hours the mixture is worked up in a manner similar to Example 8a.

Yield 16.5 g (87%)

1b. H D-Ser(Ac$_4$-$\beta$-D-Glc)-OH.HCl 9.31 g of Z-D-Ser(Ac$_4$-$\beta$-D-Glc)-OBzl are dissolved in a mixture of 100 ml of ethyl acetate and 100 ml of methanol and hydrogenated 3 hours in the presence of 9.3 g of palladium/charcoal (10%) with simultaneous addition of methanolic HCl solution (1.125 g of HCl). After filtering off the catalyst and rinsing with methanol the solution is evaporated in vacuo. The crystalline residue is recrystallized from ethyl acetate.

Yield 6.18 g (87.1%); $[\alpha]_D^{20} = -32.5°$ (c=1, in water).

1c. Z-D-Ser(Ac$_4$-β-D-Glc)-OH

To a solution of 5.08 g (10 mmol) of H-D-Ser(Ac$_4$-β-D-Glc)OH.HCl in a mixture of 15 ml of dimethylformamide and 15 ml of water, 2.6 ml of N-ethylmorpholine and 3 g of Z-ONSu are added. The mixture is stirred for about 24 hours at room temperature and then acidified with 25 ml of 1N HCl and diluted with water. The precipitate is filtered off with suction and recrystallized from ethyl acetate/petroleum ether.

Yield 5.93 g (97.8%); melting point 159°–162° C., $[\alpha]_D^{24} = -37.1°$ (c=1, in methanol)

1d. Z-D-Ser(Ac$_4$-β-D-Glc)-Leu-Arg-Pro-NH-C$_2$H$_5$-tosylate

To a solution of 1.82 g (3 mmol) of Z-D-Ser(Ac$_4$-β-D-Glc)OH, 2.27 g of H-Leu-Arg-Pro-NH-C$_2$H$_5$-ditosylate and 0.4 g of HOBt in 10 ml of dimethylformamide, 0.4 ml of N-ethylmorpholine and 660 mg of DCC are added at 0° C. The mixture is stirred one hour at 0° C. and then stood at room temperature. After about 24 hours, the precipitate is filtered off with suction and the filtrate is concentrated. The residue is dissolved in n-pentanol and successively shaken twice with concentrated water containing NaCl and three times with saturated aqueous NaHCO$_3$ solution. The organic phase is concentrated and the residue is dissolved hot in ethyl acetate. The substance is then precipitated with diethyl ether. The precipitate is filtered off with suction and washed with ether.

Yield 2.49 g (83%), melting point 104°–112° C. (with decomposition), $[\alpha]_D^{24} = -43°$ (c=1, in methanol).

1e. Z-Trp-Ser-Tyr-D-Ser(Ac$_4$-β-D-Glc)-Leu-Arg.Pro-NH-C$_2$H$_5$.HCl 2.3 g (2.3 mmol) of Z-D-Ser(Ac$_4$-β-D-Glc)-Leu-Arg-Pro-NH-C$_2$H$_5$ tosylate in methanol are catalytically hydrogenated with hydrogen in the autotitrator (addition of 1N methanolic HCl) at pH 4.5 with addition of Pd catalyst. After the end of the reaction, the catalyst is filtered off with suction and the filtrate is concentrated. The residue is triturated with ethyl acetate.

Yield 1.44 g (67%).

1.4 g of the substance above obtained (1.5 mmol of H-D-Ser-(Ac$_4$-β-D-Glc)-Leu-Arg-Pro-NH-C$_2$H$_5$.2HCl) are dissolved together with 0.88 g of Z-Trp-Ser-Tyr-OH and 0.244 g of HOObt in 6 ml of dimethylformamide. 0.2 ml of N-ethylmorpholine and 330 mg of DCC are added at 0° C., and the reaction is continued in a similar manner to Example 1d. The substance is insoluble in ethyl acetate and is therefore merely triturated with ethyl acetate. The substance is purified by dissolving in methanol, adding methanolic HCl until weakly acidic and precipitating with ethyl acetate.

Yield 1.3 g of amorphous substance, $[\alpha]_D^{22} = -42°$ (c=1, in methanol).

1f. H-Trp-Ser-Tyr-D-Ser(Ac$_4$-β-D-Glc)-Leu-Arg-Pro-NH-C$_2$H$_5$.2HCl 1.2 g of Z-Trp-Ser-Tyr-D-Ser(Ac$_4$-β-D-Glc)-Leu-Arg-Pro-NH-C$_2$H$_5$.HCl are catalytically hydrogenated in a similar manner to Example 1e.

Yield 1.06 g; $[\alpha]_D^{22} = -36.3°$ (c=1, in methanol)

1g. Pgl-His-Trp-Ser-Tyr-D-Ser(β-D-Glc)-Leu-Arg-Pro-NH-C$_2$H$_5$ acetate

To a solution of 0.55 g (0.5 mmol) of H-Trp-Ser-Tyr-D-Ser-(Ac$_4$-β-D-Glc)-Leu-Arg-Pro-NH-C$_2$H$_5$.2HCl, 0.22 g of Pgl-His(Dnp)-OH and 81 mg of HOObt in 3 ml of dimethylacetamide, 0.065 ml of N-ethylmorpholine and 0.11 g of DCC are added at 0° C. The mixture is stirred for one hour at 0° C. and then stood at room temperature. After about 20 hours, 0.25 ml of hydrazine hydrate is added. The precipitate is filtered off with suction. The filtrate is dropped into about 100 ml of ethyl acetate. The precipitate is filtered off with suction and reprecipitated from methanol/ethyl acetate. The precipitated deposit is filtered off and washed with ethyl acetate. For conversion into the acetate the compound is dissolved in water and stirred with a weakly basic ion exchanger in the acetate form. The exchanger is filtered off and the filtrate is freeze-dried.

Yield 500 mg.

It is purified on alkylated dextran gels.

Yield 210 mg; $[\alpha]_D^{26} = -42.3°$ (c=1, in water)

EXAMPLE 2

Pgl-His-Trp-Ser-Tyr-D-Ser(α-D-Man)-Leu-Arg-Pro-NH-C$_2$H$_5$

2a. Z-D-Ser(Ac$_4$-α-D-Man)-OBzl

Z-D-Ser-OBzl is reacted with 2,3,4,6-tetra-O-acetyl-α-D-mannopyranosyl bromide in a similar manner to Example 1a.

2b. H-D-Ser(Ac$_4$-α-D Man)-OH.HCl

Z-D-Ser(Ac$_4$-α-D-Man)-OBzl is hydrogenated in a similar manner to Example 1b.

$[\alpha]_D^{20} = +42.3°$ (c=1, in water).

2c. Z-D-Ser(Ac$_4$-α-D-Man)-OH 4.97 g (9 mmol) of H-D-Ser(Ac$_4$-α-D-Man)-OH.HCl are reacted in a similar manner to Example 1c with 2.34 g of N-ethylmorpholine and 2.7 g of Z-ONSu. The mixture is concentrated and the residue is partitioned between water (acidified with KHSO$_4$ to pH 3) and ethyl acetate. The ethyl acetate phase is dried over Na$_2$SO$_4$ and concentrated. 4.9 g (89%) of an oil remain. The substance does not crystallize.

2d. Z-D-Ser(Ac$_4$-α-D-Man)-Leu-Arg-Pro-NH-C$_2$H$_5$ 4.9 g (8 mmol) of Z-D-Ser(Ac$_4$-α-D-Man)-OH are reacted in a similar manner to Example 1 d with 6.05 g of H-Leu-Arg-Pro-NH-C$_2$H$_5$ ditosylate. The substance is precipitated from ethyl acetate/ether.

Yield 5.55 g, melting point 96°–102° C. (with decomposition), $[\alpha]_D^{24} = -23.5°$ (c=1, in methanol).

2e. H-D-Ser(Ac$_4$-β-D-Man)-Leu-Arg-Pro-NH-C$_2$H$_5$.2HCl 5 g of Z-D-Ser(Ac$_4$-α-D-Man)-Leu-Arg-Pro-NH-C$_2$H$_5$ are catalytically hydrogenated in a similar manner to Example 1e.

Yield 3.45 g; melting point 55°–66° C. (with decomposition), $[\alpha]_D^{24} = -26.4°$ (c=1, in methanol).

2f. Z-Trp-Ser-Tyr-D-Ser(Ac$_4$-α-D-Man)-Leu-Arg-Pro-NH-C$_2$H$_5$ 2.81 g (3 mmol) of H-D-Ser(Ac$_4$-α-D-Man)-Leu-Arg-Pro-NH-C$_2$H$_5$.2HCl are reacted in a similar manner to Example 1e with 1.76 g of Z-Trp-Ser-Tyr-OH.

Yield 3.45 g, amorphous; $[\alpha]_D^{23} = -22.1°$ (c=1, in methanol).

2g. H-Trp-Ser-Tyr-D-Ser(Ac$_4$-α-D-Man)-Leu-Arg-Pro-NH-C$_2$H$_5$.2HCl 3 g of Z-Trp-Ser-Tyr-D-Ser(Ac$_4$-α-D-Man)-Leu-Arg-Pro-NH-C$_2$H$_5$ are catalytically hydrogenated in a similar manner to Example 1e.

Yield 2.4 g; melting point 160°–162° C. (with decomposition); [α]$_D^{23}$ = −20.9° (c=1, in methanol).

2h. Pgl-His-Trp-Ser-Tyr-D-Ser(α-D-Man)-Leu-Arg-Pro-NH-C$_2$H$_5$-acetate 1.1 g (1 mmol) of H-Trp-Ser-Tyr-D-Ser(Ac$_4$-α-D-Man)-Leu-Arg-Pro-NH-C$_2$H$_5$.2HCl are reacted in a similar manner to Example 1g with 0.45 g of Pgl-His(Dnp)-OH.

Crude yield as the acetate: 870 mg.

Yield after chromatographic purification: 535 mg, amorphous; [α]$_D^{22}$ = −31.4° (c=1, in water).

EXAMPLE 3

Pgl-His-Trp-Ser-Tyr-D-Ser(β-L-Fuc)-Leu-Arg-Pro-NH-C$_2$H$_5$ and
Pgl-His-Trp-Ser-Tyr-D-Ser(Ac-β-L-Fuc)-Leu-Arg-Pro-NH-C$_2$H$_5$ 3a. Fmoc-D-Ser(Ac$_3$-β-L-Fuc)-OBzl Fmoc-D-Ser-OBzl and 2,3,4-tri-O-acetyl-α-L-fucopyranosyl bromide are reacted with one another in a similar manner to Example 8a.

3b. Fmoc-D-Ser(Ac$_3$-β-L-Fuc)-OH

Fmoc-D-Ser(Ac$_3$-β-L-Fuc)-OBzl is catalytically hydrogenated in a similar manner to Example 8b.

[α]$_D^{20}$ = −0.4° (c=1, in ethyl acetate).

3c. Fmoc-D-Ser(Ac$_3$-β-L-Fuc)-Leu-Arg-Pro-NH-C$_2$H$_5$-tosylate 4.19 g (7 mmol) of Fmoc-D-Ser-(Ac$_3$-β-L-Fuc)-OH are reacted in a similar manner to Example 1d with 5.29 g of H-Leu-Arg-Pro-NH-C$_2$H$_5$ ditosylate. The substance is precipitated from ethyl acetate/ether.

Yield 6.87 g, amorphous substance; [α]$_D^{23}$ = −30.6° (c=1, in methanol).

3d. H-D-Ser(Ac$_3$-β-L-Fuc)-Leu-Arg-Pro-NH-C$_2$H$_5$-tosylate 5.9 g (about 5 mmol) of Fmoc-D-Ser(Ac$_3$-β-L-Fuc)-Leu-Arg-Pro-NH-C$_2$H$_5$ tosylate are dissolved in 10 ml of dimethylformamide. 0.5 ml (50 mmol) of diethylamine is added and the mixture allowed to stand 1.5 hours, concentrated and triturated with ether.

Yield 4.6 g, amorphous substance; [α]$_D^{23}$ = −39.3° (c=1, in methanol.

3e. Z-Trp-Ser-Tyr-D-Ser(Ac$_3$-β-L-Fuc)-Leu-Arg-Pro-NH-C$_2$H$_5$-tosylate

To a solution of 3.84 g (4 mmol) of H-D-Ser(Ac$_3$-β-L-Fuc)-Leu-Arg-Pro-NH-C$_2$H$_5$ tosylate, 2.35 g of Z-Trp-Ser-Tyr-OH and 0.652 g of HOObt in 20 ml of dimethylformamide, 0.88 g of DCC are added at 0° C. The solution is stirred one hour at 0° C. and then allowed to come to room temperature. After about 24 hours the precipitate is filtered off with suction and the filtrate is concentrated. The residue is triturated with ethyl acetate, filtered off with suction and reprecipitated from methanol/ether.

Yield 5.58 g, amorphous; [α]$_D^{23}$ = −28.6° (c=1, in methanol).

3f. H-Trp-Ser-Tyr-D-Ser(Ac$_3$-β-L-Fuc)-Leu-Arg-Pro-NH-C$_2$H$_5$-tosylate.HCl 4.6 g of Z-Trp-Ser-Tyr-D-Ser(Ac$_3$-β-L-Fuc)-Leu-Arg-Pro-NH-C$_2$H$_5$ tosylate is catalytically hydrogenated in a similar manner to Example 1e.

Yield 3.94 g, amorphous; [α]$_D^{23}$ = −24° (c=1, in methanol).

3g. Pgl-HiB-Trp-Ser-Tyr-D-Ser(β-L-Fuo)-Leu-Arg-Pro-NH-C$_2$H$_5$-acetate and Pgl-HiB-Trp-Ser-Tyr-D-Ser(Ac-β-L-Fuc)-Leu-Arg-Pro-NH-CH$_2$H$_5$-acetate.

1.28 g of H-Trp-Ser-Tyr-D-Ser(Ac$_3$-β-L-Fuc)-Leu-Arg-Pro-NH-C$_2$H$_5$ tosylate.HCl and 0.45 g of Pgl-His(Dnp)-OH (1 mmol) are reacted in a similar manner to Example 1g.

Yield of crude acetate: 825 mg.

After chromatographic purification two fractions and a mixed fraction are obtained:

1st fraction: 181 mg Pgl-His-Trp-Ser-Tyr-D-Ser(Ac-β-L-Fuc)-Leu-Arg-Pro-NH-C$_2$H$_5$-acetate,
[α]$_D^{26}$ = −33.7° (c=1, in water);

2nd fraction: 211 mg Pgl-His-Trp-Ser-Tyr-D-Ser (β-L-Fuc)-Leu-Arg-Pro-NH-C$_2$H$_5$-acetate;
[α]$_D^{26}$ = −36.8° (c=1, in water);

Mixed fraction of both compounds: 277 mg.

EXAMPLE 4

Pgl-His-Trp-Ser-Tyr-D-Ser(β-D-Xyl)-Leu-Arg-Pro-NH-C$_2$H$_5$

4a. Fmoc-D-Ser(Ac$_3$-β-D-Xyl)-OBzl

Fmoc-D-Ser-OBzl is reacted with 2,3,4-tri-O-acetyl-α-D-xylopyranosyl bromide in a similar manner to Example 8a.

4b. Fmoc-D-Ser(Ac$_3$-β-D-Xyl)-OH

Fmoc-D-Ser(Ac$_3$-β-D-Xyl)-OBzl is catalytically hydrogenated in a similar manner to Example 8b.

[α]$_D^{20}$ = −46.8° (c=1, in ethyl acetate).

4c. H-D-Ser(Ac$_3$-β-D-Xyl)-Leu-Arg-Pro-NH-C$_2$H$_5$-tosylate 4.1 g (7 mmol) of Fmoc-D-Ser(Ac$_3$-β-D-Xyl)-OH are reacted in a similar manner to Example 1d with 5.3 g of H-Leu-Arg-Pro-NH-C$_2$H$_5$ ditosylate and the foamy residue is treated with 1.4 ml of diethylamine in 20 ml of dimethylformamide in a similar manner to Example 3d.

Yield 7 g.

For purification the substance is partitioned between ethyl acetate and water. The aqueous phase is freeze-dried.

Yield 5.28 g, amorphous; [α]$_D^{23}$ = −71.6° (c=1, in water).

4d. Z-Trp-Ser-Tyr-D-Ser(Ac$_3$-β-D-Xyl)-Leu-Arg-Pro-NH-C$_2$H$_5$-tosylate 2.8 g (3 mmol) of H-D-Ser(Ac$_3$-β-D-Xyl)-Leu-Arg-Pro-NH-C$_2$H$_5$ tosylate are reacted with 1.78 g of Z-Trp-Ser-Tyr-OH in a similar manner to Example 3e.

Yield 2.9 g, amorphous; [α]$_D^{23}$ = −47.5° (c=1, in methanol).

4e. H-Trp-Ser-Tyr-D-Ser(Ac$_3$-β-D-Xyl)-Leu-Arg-Pro-NH-C$_2$H$_5$-ditosylate 2.0 g cf Z-Trp-Ser-Tyr-D-Ser(Ac$_3$-β-D-Xyl)-Leu-Arg-Pro-NH-C$_2$H$_5$ tosylate in 35 ml of methanol (addition of 1N methanolic p-toluenesulfonic acid) are catalytically hydrogenated with hydrogen at pH 4.5 with the addition of Pd catalyst. After the end of the reaction the catalyst is filtered off, the filtrate is concentrated and the residue is triturated with ethyl acetate. The precipitate is filtered off and dried.

Yield 1.64 g, amorphous; [α]$_D^{23}$ = −42.1° (c=1, in methanol).

4f. Pgl-His-Trp-Ser-Tyr-D-Ser(β-D-Xyl)-Leu-Arg-Pro-NH-C$_2$H$_5$-acetate 1.54 g (1 mmol) of H-Trp-Ser-Tyr-D-Ser(Ac$_3$-β-D-Xyl)-Leu-Arg-Pro-NH-C$_2$H$_5$ ditosylate are reacted in a similar manner to Example 1 g with 0.45 g of Pgl-His(Dnp)-OH.

Yield as crude acetate: 1.03 g.
Yield after chromatographic purification: 737.3 mg; $[\alpha]_D^{26} = -46.5°$ (c=1, in water).

EXAMPLE 5

Pgl-His-Trp-Ser-Tyr-D-Ser(β-L-Rha)-Leu-Arg-Pro-NH-C₂H₅ and
Pgl-His-Trp-Ser-Tyr-D-Ser(Ac-α-L-Rha)-Leu-Arg-Pro-NH-C₂H₅

5a. Fmoc-D-Ser(Ac₃-α-L-Rha)-OBzl
In a similar manner to Example 8a Fmoc-D-Ser-OBzl is reacted with 2,3,4-tri-O-acetyl-α-L-rhamnopyranosyl bromide.

5b. Fmoc-D-Ser(Ac₃-α-L-Rha)-OH
Fmoc-D-Ser(Ac3-α-L-Rha)-OBzl is catalytically hydrogenated in a similar manner to Example 8b.
$[\alpha]_D^{20} = -37.9°$ (c=1, in ethyl acetate).

5c. H-D-Ser(Ac₃-α-L-Rha)-Leu-Arg-Pro-NH-C₂H₅-tosylate
4.2 g (7 mmol) of Fmoc-D-Ser(Ac3-α-L-Rha)-OH are reacted in a similar manner to Example 1d with 5.3 g of H-Leu-Arg-Pro-NH-C₂H₅ ditosylate.
The foamy residue is reacted in a similar manner to Examples 3d and 4e and purified.
Yield 5.52 g, amorphous; $[\alpha]_D^{26} = -77.6°$ (c=1, in water).

5d. Z-Trp-Ser-Tyr-D-Ser(Ac₃-α-L-Rha)-Leu-Arg-Pro-NH-C₂H₅-tosylate
3.8 g (4 mmol) of H-D-Ser(Ac₃-α-L-Rha)-Leu-Arg-Pro-NH-C₂H₅ tosylate are reacted in a similar manner to Example 3e with 2.36 g of Z-Trp-Tyr-OH.
Yield 5.2 g, amorphous; $[\alpha]_D^{26} = -49.2°$ (c=1, in methanol).

5e. H-Trp-Ser-Tyr-D-Ser(Ac₃-α-L-Rha)-Leu-Arg-Pro-NH-C₂H₅-ditosylate
4.54 g (3 mmol) of Z-Trp-Ser-Tyr-D-Ser(Ac₃-α-L-Rha)-Leu-Arg-Pro-NH-C₂H₅ tosylate are catalytically hydrogenated in a similar manner to Example 4e.
Yield 4.2 g amorphous; $[\alpha]_D^{26} = -46.7°$ (c=1, in methanol)

5f. Pgl-His-Trp-Ser-Tyr-D-Ser(β-L-Rha)-leu-Arg-Pro-NH-C₂H₅-acetate and Pgl-His-Trp-Ser-Tyr-D-Ser-(Ac-α-L-Rha)-Leu-Arg-Pro-NH-C₂H₅-acetate
1.55 g (1 mmol) of H-Trp-Ser-Tyr-D-Ser(Ac₃-α-L-Rha)-Leu-Arg-Pro-NH-C₂H₅ ditosylate are reacted in a similar manner to Example 1g with 0.45 g of Pgl-His(Dnp)-OH.
Yield as crude acetate: 1.056 g.
After chromatographic purification:
1st fraction: 378 mg Pgl-His-Trp-Ser-Tyr-D-Ser(Ac-α-L-Rha)-Leu-Arg-Pro-NH-C₂H₅-acetate;
$[\alpha]_D^{25} = -46.8°$ (c=1, in water );
2nd fraction: 287 mg Pgl-His-Trp-Ser-Tyr-D-Ser(α-L-Rha)-Leu-Arg-Pro-NH-C₂H₅-acetate;
$[\alpha]_D^{25} = -51.1°$ (c=1, in water );
Mixed fraction: 117.1 mg

EXAMPLE 6

Pgl-His-Trp-Ser-Tyr
D-Trp-Ser(β-D-Glc)-Arg-Pro-NH-C₂H₅ and
Pgl-His-Trp-Ser-Tyr-D-Trp-Ser(Ac-β-D-Glo)-Arg-Pro-NH-C₂H₅

6a. Fmoc-Ser(Ac₄-β-D-Glc)-OBzl
In a similar manner to Example 8a Fmoc-Ser-OBzl is reacted with 2,3,4,6-tetra-O-acetyl-α-D-glucopyranosyl bromide.

6b. Fmoc-Ser(Ac₄-β-D-Glc)-OH
Fmoc-Ser(Ac₄-β-D-Glc)-OBzl is catalytically hydrogenated in a similar manner to Example 8b.
$[\alpha]_D^{20} = -6.1°$ (c=1, in ethyl acetate)

6c. H-Ser(Ac₄-β-D-Glc)-Arg-Pro-NH-C₂H₅-tosylate
4.6 g (7 mmol) of Fmoc-Ser(Ac₄-β-D-Glc)-OH are reacted in a similar manner to Example 1d with 4.5 g of H-Arg-Pro-NH-C₂H₅ ditosylate. The foamy residue is reacted in a similar manner to Examples 3d and 4c. In this case, however, it must be allowed to react for longer (3 hours).
Yield 3.25 g 6d. Fmoc-D-Trp-Ser(A₄-β-D-Glc)-Arg-Pro-NH-C₂H₅-tosylate
To a solution of 1.5 g of Fmoc-D-Trp-OH (3.5 mmol), 3.6 g of H-Ser(Ac₄-β-D-Glc)-Arg-Pro-NH-C₂H₅ tosylate and 0.47 g of HOBt in 20 ml of dimethylformamide, 770 mg of DCC are added at 0°, the mixture is stirred for one hour at 0° C. and then allowed to come to room temperature. After about 24 hours the precipitate is filtered off with suction and the filtrate is concentrated. The residue is partitioned between n-pentanol and water. The organic phase is then shaken with saturated aqueous NaHCO₃ solution and water and concentrated. The residue is triturated with petroleum ether, filtered off with suction and dried.
Yield 4.38 g, amorphous; $[\alpha]_D^{23} = -29.0°$ (c=1, in methanol).

6e. H-D-Trp-Ser(Ac₄-β-D-Glc)-Arg-Pro-NH-C₂H₅-tosylate
4 g of Fmoc-D-Trp-Ser(Ac₄-β-D-Glc)-Arg-Pro-NH-C₂H₅ tosylate are reacted in a similar manner to Examples 3d and 4c.
Yield 2.5 g; $[\alpha]_D^{25} = -69.2°$ (c=1, in water).

6f. Z-Trp-Ser-Tyr-D-Trp-Ser(Ac₄-β-D-Glo)-Arg-Pro-NH-C₂H₅-tosylate
1.18 g (2 mmol) of Z-Trp-Ser-Tyr-OH are reacted in a similar manner to Example 3e with 1.8 g of H-D-Trp-Ser(Ac₄-β-D-Glc)-Arg-Pro-NH-C₂H₅ tosylate. The substance is then precipitated from n-pentanol/ether.
Yield 2.35 g, amorphous; $[\alpha]_D^{25} = -33.4°$ (c=1, in methanol).

6g. H-Trp-Ser-Tyr-D-Trp-Ser(Ac₄-β-D-Glc)-Arg-Pro-NH-C₂H₅-tosylate.HCl
2.2 g of Z-Trp-Ser-Tyr-D-Trp-Ser(Ac₄-β-D-Glc)-Arg-Pro-NH-C₂H₅ tosylate are catalytically hydrogenated in a similar manner to Example 1e.
Yield 1.78 g, amorphous; $[\alpha]_D^{23} = -30.0°$ (c=1, in methanol).

6h. Pgl-His-Trp-Ser-Tyr-D-Trp-Ser(β-D-Glc)-Arg-Pro-NH-C₂H₅-acetate and Pgl-His-Trp-Ser-Tyr-D-Trp-Ser(Ac-β-D-Glc)-Arg-Pro-NH-C₂H₅-acetate
0.45 g (1 mmol) of Pl-His(Dnp)-OH is reacted in a similar manner to Example 1 g with 1.43 g of H-Trp-Ser-Tyr-D-Trp-Ser(Ac₄-β-D-Glc)-Arg-Pro-NH-C₂H₅ tosylate.HCl.
Yield as crude acetate: 939 mg.
After chromatographic purification:
1st fraction: 332 mg Fgl-His-Trp-Ser-Tyr-D-Trp-Ser(β-D-Glc)-Arg-Pro-NH-C₂H₅-acetate; $[\alpha]_D^{26} = -56.7°$ (c=1, in water );
2nd fraction: 112 mg Pgl-Hia-Trp-Ser-Tyr-D-Trp-Ser(Ac-β-D-Glc)-Arg-Fro-H-C₂H₅-acetate;- $[\alpha]_D^{26} = -50.4°$ (c=1, in water);
Mixed fraction: 217 mg.

EXAMPLE 7

Pgl-His-Trp-Ser-Tyr-D-Trp-Ser($\beta$-L-Fuc)-Arg-Pro-NH-C$_2$H$_5$, Pgl-His-Trp-Ser Tyr-D-Trp-Ser(Ac-$\beta$-L-Fuc)-Arg-Pro-NH-C$_2$H$_5$ and Pgl-His-Trp-Ser-Tyr-D-Trp-Ser(Ac$_2$-$\beta$-L-Fuc)-Arg-Pro-NH-C$_2$H$_5$ 7.a Fmoc-Ser(Ac$_3$-$\beta$-L-Fuc)-OBzl In a similar manner to Example 8a Fmoc-Ser-OBzl is reacted with 2,3,4-tri-O-acetyl-$\alpha$-L-fucopyranosyl bromide.

7b. Fmoc-Ser(Ac$_3$-$\beta$-L-Fuc)-OH Fmoc-Ser(Ac$_3$-$\beta$-L-Fuc)-OBzl is catalytically hydrogenated in a similar manner to Example 8b.

$[\alpha]_D^{20} = +17.1°$ (c=1, in ethyl acetate).

7c. H-Ser(Ac$_3$-$\beta$-L-Fuc) Arg-Pro-NH-C$_2$H$_5$-tosylate 4.2 g (7 mmol) of Fmoc-Ser(Ac$_3$-$\beta$-L-Fuc)-OH are reacted in a similar manner to Example 1d with 4.5 g of H-Arg-Pro-NH-C$_2$H$_5$ ditosylate. The resulting foam is reacted in a similar manner to Example 6c with 0.7 ml of diethylamine in 20 ml of dimethylformamide.

Yield 3.07 g; $[\alpha]_D^{25} = -22.8°$ (c=1, in water).

7.d Fmoc-D-Trp-Ser(Ac$_3$-$\beta$-L-Fuc)-Arg-Pro-NH-C$_2$H$_5$-tosylate 1.5 g (3.5 mmol) of Fmoc-D-Trp-OH are reacted in a similar manner to Example 6d with 2.9 g of H-Ser(Ac$_3$-$\beta$-L-Fuc)-Arg-Pro-NH-C$_2$H$_5$ tosylate.

Yield 3.65 g, amorphous; $[\alpha]_D^{22} = -12.8°$ (c=1, methanol).

7.e. H-D-Trp-Ser(Ac$_3$-$\beta$-L-Fuc) Arg-Pro-NH-C$_2$H$_5$-tosylate 3.5 g (2.8 mmol) c& Fmoc-D-Trp-Ser(Ac$_3$-$\beta$-L-Fuc)-Arg-Pro-NH-C$_2$H$_5$ tosylate are reacted in a similar manner to Examples 3d and 4c.

Yield 1.81 g, amorphous; $[\alpha]_D^{22} = -48.2°$ (c=1, in water).

7f. Z-Trp-Ser-Tyr-D-Trp-Ser(Ac$_3$-$\beta$-L-Fuo)-Arg-Pro-NH-C$_2$H$_5$-tosylate 0.89 g (1.5 mmol) o& Z-Trp-Ser-Tyr-OH is reacted in a similar manner to Example 3e with 1.52 g of H-D-Trp-Ser(Ac$_3$-$\beta$-L-Fuc)-Arg-Pro-NH-C$_2$H$_5$ tosylate.

Yield 2.1 g, amorphous; $[\alpha]_D^{22} = -28.5°$ (c=1, in methanol).

7g. H-Trp-Ser-Tyr-D-Trp-Ser(Ac$_3$-$\beta$-1-Fuc)-Arg-Pro-NH-C$_2$H$_5$-ditosylate 1.9 g (1.2 mmol) cf Z-Trp-Ser-Tyr-D-Trp-Ser(Ac$_3$-$\beta$-L-Fuc)-Arg-Pro-NH-C$_2$H$_5$ tosylate are catalytically hydrogenated in a similar manner to Example 4e.

Yield 1.71 g, amorphous; $[\alpha]_D^{22} = -45.6°$ (c=1, in water). 7h. Pgl-His-Trp-Ser-Tyr-D-Trp-Ser($\beta$-L-Fuc)-Arg-Pro-NH-C$_2$H$_5$-acetate Pgl-His-Trp-Ser-Tyr-D-Trp-Ser(Ac-$\beta$-L-Fuc)-Arg-Pro-NH-C$_2$H$_5$-acetate and Pgl-His-Trp-Ser-Tyr-D-Trp-Ser(Ac$_2$-$\beta$L-Fuc)-Arg-Pro-NH-C$_2$H$_5$-acetate 0.45 g (1 mmol) of Pgl-His(Dnp)-OH is reacted in a similar manner to Example 1g with 1.62 g of H-Trp-Ser-Tyr-D-Trp-Ser-(Ac$_3$-$\beta$-L-Fuc)-Arg-Pro-NH-C$_2$H$_5$ ditosylate.

Yield as crude acetate: 1.23 g.

After chromatographic purification:

1st fraction: 111.6 mg Pgl-His-Trp-Ser-Tyr-D-Trp-Ser(Ac$_2$-$\beta$-L-Fuc)-Arg-Pro-NH-C$_2$H$_5$-acetate; $[\alpha]_D^{26} = 43.3°$ (c=1, in water);

2nd fraction: 239.7 mg Pgl-His-Trp-Ser-Tyr-D-Trp-Ser(Ac-$\beta$-L-Fuc)-Arg-Pro-NH-C$_2$H$_5$-acetate;- $[\alpha]_D^{26} = -49.7°$ (c=1, in water );

3rd fraction: 97.9 mg Pgl-His-Trp-Ser-Tyr-D-Trp-Ser($\beta$-L-Fuc)-Arg-Pro-NH-C$_2$H$_5$-acetate; $[\alpha]_D^{26} = -43.7°$ (c=1, in water).

EXAMPLE 8

Pgl-His-Trp-Ser-Tyr-D-Trp-Ser($\alpha$-D-Man)-Arg-Pro-NH-C$_2$H$_5$,

Pgl-His-Trp-Ser-Tyr-D-Trp-Ser(Ac-$\alpha$-D-Man)-Arg-Pro-NH-C$_2$H$_5$ and

Pgl-His-Trp-Ser-Tyr-D-Trp-Ser(Ac$_2$-$\alpha$-D-Man)-Arg-Pro-NH-C$_2$H$_5$

8a. Fmoc-Ser(Ac$_4$-$\alpha$-D-Man)-OBzl 10 g (24 mmol) of Fmoc-Ser-OBzl are dissolved in a mixture of 80 ml of toluene and 80 ml of nitromethane. After the addition of 9.8 g (24 mmol) of 2,3,4,6-tetra-O-acetyl-$\alpha$-D-mannopyranosyl bromide and 6.1 g (24 mmol) of Hg(CN)$_2$ the reaction mixture is stirred 15 hours at 40° C. The course of the glycosylation is followed by thin layer chromatography (eluting agent: dichloromethane/ethyl acetate 6:1; Merck precoated silica gel plate, GF$_{254}$; detection: ethanol/sulfuric acid 10:1 (v/v) and then heat treatment). The re-action mixture is cooled to 0° C. and washed twice with 10% aqueous potassium iodide solution, once with saturated aqueous sodium hydrogen carbonate solution and once with ice water. The organic phase is concentrated in vacuo and the remaining syrup is codistilled twice with toluene. The resulting product (24 g) is purified by column chromatography on silica gel (silica gel 60 (70–230 mesh); eluting agent: chloroform/ethyl acetate 9:1).

Yield 14.5 g (80.8%).

8b. Fmoc-Ser(Ac$_4$-$\alpha$-D-Man)-OH 4.5 g of Fmoc-Ser(Ac$_4$-$\alpha$-D-Man)-OBzl are dissolved in 100 ml of dry ethyl acetate, treated with 14.5 g of palladium/charcoal (10%) and hydrogenated at room temperature for 70 minutes. After filtering off the catalyst, the organic phase is washed once with ice water, then dried over sodium sulfate and concentrated in vacuo to a syrup. The resulting product is purified by column chromatography on 130 g of silica gel (eluting agent: dichloromethane/acetone 4:1).

Yield 11.8 g (93%); $[\alpha]_D^{20} = +37°$ (c=1, in ethyl acetate).

$^{13}$C-NMR (90 MHz, CDCl$_3$): $\delta$ = 172.97 (COOH); 170.67 (2.x CO, Ac); 170.25 (CO, Ac); 169.70 (CO, Ac); 156.15 (CO, Ureth): 143.75+141.15+127.66+127.61+125.06+119.91 (Aryl, Fmoc); 98.02 (C-1. Man); 69.41 (CH, Fmoc): 69.41+68.87 (2×C)+67.30+66.05 (C-2, C-3, C-4, C-5, C-6, Man): 62.26 (CH$_2$, Ser); 54.40 (CH, Ser); 47.04 (CH$_2$, Fmoc); 20.70 (2×C)+20.59 (2×C) (CH$_3$, Ac).

8c. H-Ser(Ac$_4$-$\alpha$-D-Man)-Arg-Pro-NH -C$_2$H$_5$-tosylate 4.6 g (7 mmol) of Fmoc-Ser(Ac$_4$-$\alpha$-D-Man)-OH are reacted in a similar manner to Example 1d with 4.5 g of H-Arg-Pro-NH-C$_2$H$_5$ ditosylate.

The resulting foam is reacted in a similar manner to Example 6d.

Yield 6.24 g, amorphous; $[\alpha]_D^{22} = -9.2°$ (c=1, in water).

8d. Fmoc-D-Trp-Ser(Ac$_4$-$\alpha$-D-Man)-Arg-Pro-NH-C$_2$H$_5$-tosylate 2.15 g (5 mmol) of Fmoc-D-Trp-OH are reacted in a similar manner to Example 6d with 4.44 g of H-Ser-(Ac$_4$-$\alpha$-D Man)-Arg-Pro-NH-C$_2$H$_5$ tosylate.

Yield 5.75 g, amorphous; $[\alpha]_D^{22} = -3.4°$ (c=1, in methanol).

8e. H-D-Trp-Ser-(Ac$_4$-$\alpha$-D-Man)-Arg-Pro-NH-C$_2$H$_5$-tosylate 5.19 g (4 mmol) of Fmoc-D-Trp-Ser-(Ac$_4$-$\alpha$-D-Man)-arg-Pro-NH-C$_2$H$_5$ tosylate are reacted in a similar manner to Example 3d and 4c.

Yield 3.05 g, amorphous; $[\alpha]_D^{22} = -41.7°$ (c=1, in water).

8f. Z-Trp-Ser Tyr-D-Trp-Ser(Ac$_4$-$\alpha$-D-Man)-Arg-Pro-NH-C$_2$H$_5$-tosylate 1.48 g (2.5 mmol) of Z-Trp-Ser-Tyr-OH are reacted in a similar manner to Example 3e with 2.68 g of H-D-Trp-Ser(Ac$_4$-$\alpha$-D-Man)-Arg-Pro-NH-C$_2$H$_5$ tosylate.

Yield 3.55 g, amorphous; $[\alpha]_D^{22} = -17.0°$ (c=1, in methanol).

8g. H-Trp-Ser-Tyr-D-Trp-Ser(Ac$_4$-$\alpha$-D-Man)-Arg-Pro-NH-C$_2$H$_5$-ditosylate 3.3 g (2 mmol) of Z-Trp-Ser-Tyr-D-Trp-Ser(Ac$_4$-$\alpha$-D-Man)-Arg-Pro-NH-C$_2$H$_5$ tosylate are catalytically hydrogenated in a similar manner to Example 4e.

Yield 2.85 g, amorphous; $[\alpha]_D^{23} = -12.6°$ (c=1, in methanol).

8h. Pgl-His-Trp-Ser-Tyr-D-Trp-Ser($\alpha$-D-Man)-Arg-Pro-NH-C$_2$H$_5$-acetate, Pgl-His-Trp-Ser-Tyr-D-Trp-Ser(Ac-$\alpha$-D-Man)-Arg-Pro-NH-C$_2$H$_5$-acetate and Pgl-His-Trp-Ser-Tyr-D-Trp-Ser(Ac$_2$-$\beta$-D-Man)-Arg-Pro-NH-C$_2$H$_5$-acetate 0.45 g (1 mmol) of Pgl-His(Dnp)-OH are reacted in a similar manner to Example 1g with 1.68 g of H-Trp-Ser-Tyr-D-Trp-Ser-(Ac$_4$-$\alpha$-D-Man)-Arg-Pro-NH-C$_2$H$_5$ ditosylate.

Yield as crude acetate: 1.43 g.

After chromatographic purification:

1st fraction: 109.6 mg Pgl-His-Trp-Ser-Tyr-D-Trp-Ser(Ac$_2$-$\alpha$-D-Man)-Arg-Pro-NH-C$_2$H$_5$; $[\alpha]_D^{25} = -33.4°$ (c=1, in water);

2nd fraction: 346.6 mg Pgl-His-Trp-Ser-Tyr-D-Trp-Ser(Ac-$\alpha$-D-Man)-Arg-Pro-NH-C$_2$H$_5$; $[\alpha]_D^{25} = -33.6°$ (c=1, in water);

3rd fraction: 76.8 mg Pgl-His-Trp-Ser-Tyr-D-Trp-Ser($\alpha$-D-Man)-Arg-Pro-NH-C$_2$H$_5$; $[\alpha]_D^{25} = -27.5°$ (c=1, in water), Mixed fraction between fraction 1 and 2: 187.5 mg and mixed fraction between fraction 2 and 3: 76.2 mg.

EXAMPLE 9

Pgl-His-Trp-Ser-Tyr-D-Trp-Ser($\beta$-D-Xyl)-Arg-Pro-NH-C$_2$H$_5$ and

Pgl-His-Trp-Ser-Tyr-D-Trp-Ser(Ac-$\beta$-D-Xyl)-Arg-Pro-NH-C$_2$H$_5$

9a. Fmoc-Ser(Ac$_3$-$\beta$-D-Xyl)-OBzl

This is obtained in a similar manner to Example 18a from FmocSer-OBzl and 2,3,4-tri-O-acetyl-$\alpha$-D-xylopyranosyl bromide.

9b. Fmoc-Ser(Ac$_3$-$\beta$-D-Xyl)-OH

This is obtained in a similar manner to Example 18b from Fmoc-Ser(Ac$_3$-$\beta$-D-Xyl)-OBzl by catalytic hydrogenation.

$[\alpha]_D^{20} = -19.9°$ (c=1, in ethyl acetate).

9c. H-Ser(Ac$_3$-$\beta$-D-Xyl)-Arg-Pro-NH-C$_2$H$_5$-tosylate 4.1 g (7 mmol) of Fmoc-Ser(Ac$_3$-$\beta$-D-Xyl)-OH are reacted in a similar manner to Example 1d with 4.5 g of H-Arg-Pro-NH-C$_2$H$_5$ ditosylate.

The resulting foam is further treated in a manner similar to Example 6c.

Yield 4.93 g, amorphous; $[\alpha]_D^{23} = -57.0°$ (c=1, in water).

9d. Fmoc-D-Trp-Ser(Ac$_3$-$\beta$-D-Xyl)-Arg-Pro-NH-C$_2$H$_5$-tosylate 2.15 g (5 mmol) of Fmoc-D-Trp-OH are reacted in a similar manner to Example 6d with 4.08 g of H-Ser-(Ac$_3$-$\beta$-D-Xyl)-Arg-Pro-NH$_2$H$_5$ tosylate.

Yield 5.7 g, amorphous; $[\alpha]_D^{23} = -41.5°$ (c=1, in methanol).

9e. H-D-Trp-Ser(Ac$_3$-$\beta$-D-Xyl)-Arg-Pro-NH C$_2$H$_5$-tosylate 4.9 g (4 mmol) of Fmoc-D-Trp-Ser(Ac$_3$-$\beta$-D-Xyl)-Arg-Pro-NH C$_2$H$_5$ tosylate are reacted in a similar manner to Example 3d and 4c.

Yield 2.58 g, amorphous; $[\alpha]_D^{23} = -93.7°$ (c=1, in water).

9f. Z-Trp-Ser-Tyr-D-Trp-Ser(Ac$_3$-$\beta$-D-Xyl)-Arg-Pro-NH-C$_2$H$_5$-tosylate 1.48 g (2.5 mmol) of Z-Trp-Ser-Tyr-OH are reacted in a similar manner to Example 3e with 2.5 g of H-D-Trp-Ser(Ac$_3$-$\beta$-D-Xyl)-Arg-Pro-NH-C$_2$H$_5$ tosylate.

Yield 3.39 g, amorphous; $[\alpha]_D^{23} = -48.5°$ (c=1, in methanol).

9g. H-Trp-Ser-Tyr-D-Trp-Ser(Ac$_3$-$\beta$-D-Xyl)-Arg-Pro-NH-C$_2$H$_5$-ditosylate 2.78 g (2 mmol) of Z-Trp-Ser-Tyr-D-Trp-Ser(Ac$_3$-$\beta$-D-Xyl)-Arg-Pro-NH-C$_2$H$_5$ tosylate are catalytically hydrogenated in a similar manner to Example 4e.

Yield 2.5 g, amorphous; $[\alpha]_D^{25} = -46.1°$ (c=1, in methanol).

9h. Pgl-His-Trp-Ser-Tyr-D-Trp-Ser($\beta$-D-Xyl)-Arg-Pro-NH-C$_2$H$_5$-acetate and Pgl-His-Trp-Ser-Tyr-D-Trp-Ser(Ac-$\beta$-D-Xyl)-Arg-Pro-NH-C$_2$H$_5$ 0.45 g of Pgl-His(Dnp)-OH is reacted in a similar manner to Example 1g with 1.61 g of H-Trp-Ser-Tyr-D-Trp-Ser(Ac$_3$-$\beta$-D-Xyl)-Arg-Pro-NH-C$_2$H$_5$ ditosylate.

Yield as crude acetate: 0.9344 g.

Yield after chromatographic purification:

1st fraction: 407.3 mg Pgl-His-Trp-Ser-Tyr-D-Trp-Ser($\beta$-D-Xyl)-Arg-Pro-NH-C$_2$H$_5$-acetate; $[\alpha]_D^{25} = -59.7°$ (c=1, in water) and 2nd fraction: 90.3 mg Pgl-His-Trp-Ser-Tyr-D-Trp-Ser(Ac-$\alpha$-D-Xyl)-Arg-Pro-NH-C$_2$H$_5$-acetate; $[\alpha]_D^{25} = -56.6°$ (c=1, in water).

EXAMPLE 10

Pgl-His-Trp-Ser-Tyr-D-Trp-Ser($\alpha$-L-Rha)-Arg-Pro-NH-C$_2$H$_5$

Pgl-His-Trp-Ser-Tyr-D-Trp-Ser(Ac-$\alpha$-L-Rha)-Arg-Pro-NH-C$_2$H$_5$

10a. Fmoc-Ser(Ac$_3$-$\alpha$-L-Rha)-OBzl

Fmoc-Ser-OBzl and 2,3,4-tri-O-acetyl-$\alpha$-L-rhamnopyranosyl bromide are reacted in a similar manner to Example 8a.

10b. Fmoc-Ser(Ac$_3$-$\alpha$-L-Rha)-OH

Fmoc-Ser(Ac$_3$-$\alpha$-L-Rha)-OBzl is hydrogenated in a similar manner to Example 8b.

$[\alpha]_D^{20} = -28.7°$ (c=1, in ethyl acetate).

10c. H-Ser(Ac$_3$-$\alpha$-L-Rha)-Arg-Pro-NH-C$_2$H$_5$-tosylate 4.2 g (7 mmol) of Fmoc-D-Ser(Ac$_3$-$\alpha$L-Rha)-OH are reacted in a similar manner to Example 1d with 4.5 g of H-Arg-Pro-NH-C$_2$H$_5$ditosylate.

The resulting foam is worked up in a similar manner to Example 6c.

Yield 4.83 g, amorphous; $[\alpha]_D^{26} = -61.4°$ (c=1, in water).

10d. Fmoc-D-Trp-Ser(Ac₃-α-L-Rha)-Arg-Pro-NH-C₂H₅-tosylate 2.14 g (5 mmol) of Fmoc-D-Trp-OH are reacted in a similar manner to Example 6d with 5.15 g of H-Ser-(Ac₃-α-L-Rha)-Arg-Pro-NH-C₂H₅ tosylate.

Yield 5.85 g, amorphous; $[\alpha]_D^{26} = -38.8°$ (c=1, in methanol).

10e. H-D-Trp-Ser(Ac₃-α-L-Rha)-Arg-Pro-NH-C₂H₅-tosylate 4.95 g (4 mmol) of Fmoc-D-Trip-Ser(Ac₃-α-L-Rha)-Arg-Pro-NH-C₂H₅ tosylate are reacted in a similar manner to Examples 3d and 4c.

Yield 2.72 g, amorphous; $[\alpha]_D^{26} = -95.8°$ (c=1, in water).

10f. Z-Trp-Ser-Tyr-D-Trp-Ser(Ac₃-α-L-Rha)-Arg-Pro-NH-C₂H₅-tosylate 1.48 g (2.5 mmol) of Z-Trp-Ser-Tyr-OH are reacted in a similar manner to Example 3e with 2.54 g of H-D-Trp-Ser(Ac₃-α-L-Rha)-Arg-Pro-NH-C₂H₅ tosylate.

Yield 3.95 g, amorphous; $[\alpha]_D^{26} = -44.4°$ (c=1, in methanol).

10g. H-Trp-Ser-Tyr-D-Trp-Ser(Ac₃-α-L-Rha)-Arg-Pro-NH-C₂H₅-ditosylate 3.2 g (2 mmol) of Z-Trp-Ser-Tyr-D-Trp-Ser(Ac₃-α-L-Rha)-Arg-Pro-NH-C₂H₅ tosylate are catalytically hydrogenated in a manner similar to Example 4e.

Yield 2.87 g, amorphous; $[\alpha]_D^{26} = -42.3°$ (c=1, in methanol).

10h. Pgl-His-Trp-Ser-Tyr-D-Trp-Ser(α-L-Rha)-Arg-Pro-NH-C₂H₅-acetate and Pgl-His-Trp-Ser-Tyr-D-Trp-Ser(Ac-α-L-Rha)-Arg-Pro-NH-C₂H₅-acetate 0.45 g (1 mmol) of Pgl-His(Dnp)-OH is reacted in a similar manner to Example 1g with 1.62 g of H-Trp-Ser-Tyr-D-Trp-Ser(Ac₃-α-L-Rha)-Arg-Pro-NH-C₂H₅ ditosylate.

Yield as crude acetate: 893 mg.

Yield after chromatographic purification

1st fraction: 424.3 mg Pgl-His-Trp-Ser-Tyr-D-Trp-Ser(α-L-Rha)-Arg-Pro-NH-C₂H₅-acetate; and 2nd fraction: 95.6 mg Pgl-His-Trp-Ser-Tyr-D-Trp-Ser(Ac-α-L-Rha)-Arg-Pro-NH-C₂H₅-acetate Mixed fraction: 87.1 mg.

EXAMPLE 11

Pgl-His-Trp-Ser-Tyr-D-Ser(β-D-Gal)-Leu-Arg-Pro-NH-C₂H₅

11a. Fmoc-D-Ser(Ac₄-β-D-Gal)-OBzl

Fmoc-D-Ser-OBzl and 2,3,4,6-tetra-O-acetyl-β-D-galactopyranosyl bromide are reacted in a similar manner to Example 8a.

$[\alpha]_D^{26} = -5.9°$ (c=1, in chloroform).

11b. Fmoc-D-Ser(Ac₄-β-D-Gal)-OH

Fmoc-D-Ser(Ac₄-β-D-Gal)-OBzl is catalytically hydrogenated in a similar manner to Example 8b.

$[\alpha]_D^{26} = -5.8°$ (c=1, in chloroform).

11c. H-D-Ser(Ac₄-β-D-Gal)-Leu-Arg-Pro-NH-C₂H₅-tosylate 4.6 g (7 mmol) of Fmoc-D-Ser(Ac₄-β-D-Gal)-OH are reacted in a similar manner to Example 1d with 5.3 g of H-Leu-Arg-Pro-NH-C₂H₅ ditosylate.

The foamy residue is reacted and purified in a similar manner to Examples 3d and 4e.

Yield 5.38 g, amorphous; $[\alpha]_D^{26} = -54.5°$ (c=1, in water)

11d. H-Trp-Ser-Tyr-OH-acetate 23.55 g (40 mmol) of Z-Trp-Ser-Tyr-OH are dissolved in 700 ml of 90% aqueous acetic acid and catalytically hydrogenated with Pd/charcoal. After the end of the hydrogenation the catalyst is filtered off and the filtrate is concentrated. The residue is triturated with ether, filtered off and dried.

Yield 20.4 g; melting point 716°-181° with decomposition; $[\alpha]_D^{25} = +33.5°$ (c=1, methanol).

113. Fmoc-Trp-Ser-Tyr-OH

To a mixture of 50 ml of water and 50 ml of dioxane, 19.96 g (38.8 mmol) of H-Trp-Ser-Tyr-OH acetate, 6.52 g (77.6 mmol) of NaHCO₃ and 14.2 g (42 mmol) of Fmoc-OnSu are added successively. After allowing to stand for 4 hours at room temperature, insoluble material is filtered off and discarded next day. The filtrate is concentrated. The residue is triturated with petroleum ether, filtered off with suction and dried.

Yield 27.1 g.

For purification the substance is boiled with 400 ml of ethyl acetate and filtered off with suction after cooling.

Yield 23.1 g (88%); melting point 186°-188° C.; $[\alpha]_D^{25} = -0.4°$ (c=1, in methanol).

11f. Fmoc-Trp-Ser-Tyr-D-Ser(Ac₄-β-D-Gal)-Leu-Arg-Pro-NH-C₂H₅-tosylate 3.0 g (3 mmol) of H-D-Ser(Ac₄-β-D-Gal)-Leu-Arg-Pro-NH-C₂H₅ tosylate are reacted in a similar manner to Example 3e with 2.03 g Fmoc-Trp-Ser-Tyr-OH, 0.49 g of HOOBt and 0.66 g of DCC in 10 ml of dimethylformamide. The residue is partitioned between n-pentanol and water. The n-pentanol phase is concentrated and the residue is triturated with methyl tert.-butyl ether. The precipitate is filtered off and dried.

Yield 4.69 g; melting point 108°-110° C. with decomposition; $[\alpha]_D^{23} = -34.2°$ (c=1, in methanol).

11g. H-Trp-Ser-Tyr-D-Ser(Ac₄-β-D-Gal)-Leu-Arg-Pro-NH-C₂H₅-tosylate

To a solution of 2.98 g (2 mmol) of Fmoc-Trp-Ser-Tyr-D-Ser-(Ac₄-β-D-Gal)-Leu-Arg-Pro-NH-C₂H₅ tosylate in 15 ml of dimethylformamide, 0.2 mol (2 mmol) of diethylamine is added at room temperature and the mixture is stirred 1 hour at room temperature and concentrated. The residue is triturated with diethyl ether, filtered off with suction and dried.

Yield 2.65 g; melting point 104°-105° C. with decomposition; $[\alpha]_D^{23} = -34.5°$ (c=1, in methanol).

11h. Pgl-His-Trp-Ser-Tyr-D-Ser(β-D-Gal)-Leu-Arg-Pro-NH-C₂H₅-acetate

To a solution of 1.27 g (1 mmol) of H-Trp-Ser-Tyr-D-Ser-(Ac₄-β-D-Gal)-Leu-Arg-Pro-NH-C₂H₅ tosylate, 163 mg of HOOBt and 450 g of Pgl-His(Dnp)-OH in 6 ml of dimethylacetamide, 225 mg of DCC are added and the mixture is stirred 1 hour at 0° C. and 3 hours at room temperature, allowed to stand overnight, and 1 ml of hydrazine hydrate is added the following day. After stirring for 4 hours at room temperature, the precipitate is filtered off with suction and the filtrate is treated with ethyl acetate. The residue is filtered off with suction and reprecipitated from methanol/ethyl acetate, filtered off with suction, washed with ethyl acetate and dried.

Yield 910 mg.

In a similar manner to Example 1 g the substance is converted into the acetate: 818 mg.

Yield after chromatographic purification: 413 mg; $[\alpha]_D^{22} = -40.8°$ (c=1, in water).

EXAMPLE 12

Pgl-His-Trp-Ser-Tyr-D-Ser(L-Ara)-Leu-Arg-Pro-NH-C₂H₅

12a. Fmoc-D-Ser(Ac₃-L-Ara)-OBzl

Fmoc-D-Ser-OBzl and 2,3,4-tri-O-acetyl-L-arabinopyranosyl bromide is reacted in a similar manner to Example 8a.

$[\alpha]_D^{25} = -9.3°$ (c=1, in chloroform).

12b. Fmoc-D-Ser(Ac$_3$-L-Ara)-OH

Fmoc-D-Ser(Ac$_3$-L-Ara)-OBzl is catalytically hydrogenated in a similar manner to Example 8b.

$[\alpha]_D^{25} = -21.9°$ (C=1, in chloroform).

12c. H-D-Ser(Ac$_3$-L-Ara)-Leu-Arg-Pro-NH-C$_2$H$_5$-tosylate 4.1 g (7 mmol) of Fmoc-D-Ser(Ac$_3$-L-Ara)-OH are reacted in a similar manner to Example 1d with 5.3 g of H-Leu-Arg-Pro-NH-C$_2$H$_5$ ditosylate.

The foamy residue is reacted and purified in a similar manner to Examples 3d and 4e.

Yield 5.1 g; $[\alpha]_D^{23} = -57.5°$ (c=1, in water).

12d. Fmoc-Trp-Ser-Tyr-D-Ser(Ac$_3$-L-Ara)-Leu-Arg-Pro-NH-C$_2$H$_5$-tosylate 2.78 g (3 mmol) of H-D-Ser(Ac$_3$-L-Ara)-Leu-Arg-Pro-NH-C$_2$H$_5$ tosylate are reacted in a similar manner to Example 11f with 2.03 g of Fmoc-Trp-Ser-Tyr-OH. The precipitate is filtered off the following day and the filtrate is treated with 150 ml of water, 3 ml of saturated NaHCO$_3$ solution and 1 ml of saturated NaCl solution. As a result a precipitate is formed, which is filtered off with suction.

Yield 3.47 g; melting point 128°-131° C. with decomposition; $[\alpha]_D^{23} = -36.3°$ (c=1, in methanol).

12e. H-Trp-Ser-Tyr-D-Ser(Ac$_3$-L-Ara)-Leu-Arg-Pro-NH-C$_2$H$_5$-tosylate 2.83 g (2 mmol) of Fmoc-Trp-Ser-D-Ser(Ac$_3$-L-Ara)-Leu-Arg-Pro-NH-C$_2$H$_5$ tosylate are reacted in a similar manner to Example 11g.

Yield 2.55 g; melting point 106°-108° C. with decomposition; $[\alpha]_D^{23} = -37.6°$ (c=1, in methanol).

12f. Pgl-His-Trp-Ser-Tyr-D-Ser(L-Ara)-Leu-Arg-Pro-NH-C$_2$H$_5$-acetate 1.19 g (1 mmol) of H-Trp-Ser-Tyr-D-Ser(Ac$_3$-L-Ara)-Leu-Arg-Pro-NH-C$_2$H$_5$ tosylate are reacted in a similar manner to Example 11h.

Yield as crude acetate: 1.05 g.

Yield after chromatographic purification 362 mg; $[\alpha]_D^{22} = -46.0°$ (c=1, in water)

EXAMPLE 13

Pgl-His-Trp-Ser-Tyr-D-Ser(β-Lac)-Leu-Arg-Pro-NH-C$_2$H$_5$

13a. Fmoc-D-Ser(Ac$_7$-β-Lac)-OBzl

Fmoc-D-Ser-OBzl and 2,3,6,2',3',4',6'-hepta-O-acetyl-β-lactopyranosyl bromide are reacted in a similar manner to Example 8a.

$[\alpha]_D^{22} = -9.1°$ (c=1, in chloroform).

13b. Fmoc-D-Ser(Ac$_7$-β-Lac)-OH

Fmoc-D-Ser(Ac$_7$-β-Lac) is catalytically hydrogenated in a similar manner to Example 8d.

$[\alpha]_D^{22} = -23.7°$ (c=1, in chloroform).

13c. H-D-Ser(Ac$_7$-β-Lac)-Leu-Arg-Pro-NH-C$_2$H$_5$-tosylate 4.5 g (4.76 mmol) of Fmoc-D-Ser(Ac$_7$-β-Lac)-OH are reacted in a similar manner to Example 1d with 3.6 g (4.75 mmol) of H-Leu-Arg-Pro-NH-C$_2$H$_5$ ditosylate.

The foamy residue is reacted and purified in a similar manner to Examples 3d and 4e.

Yield 4.32 g; $[\alpha]_D^{21} = -49.5°$ (c=1, in water).

13d. Fmoc-Trp-Ser-Tyr-D-Ser(Ac$_7$-β-Lac)-Leu-Arg-Pro-NH-C$_2$H$_5$-tosylate 3.87 g (3 mmol) of H-D-Ser(Ac$_7$-β-Lac)-Leu-Arg-Pro-NH-C$_2$H$_5$ tosylate are reacted in a similar manner to Example 11f with 2.03 g of Fmoc-Trp-Ser-Tyr-OH.

Yield 5.56 g; melting point 124°-127° C. with decomposition; $[\alpha]_D^{21} = -34.5°$ (c=1, methanol).

13e. H-Trp-Ser-Tyr-D-Ser(Ac$_7$-β-Lac)-Leu-Arg-Pro-NH-C$_2$H$_5$-tosylate 3.9 g (2 mmol) of Fmoc-Trp-Ser-Tyr-D-Ser(Ac$_7$-β-Lac)-Leu-Arg-Pro-NH-C$_2$H$_5$ tosylate are reacted in a similar manner to Example 11 g.

Yield 3.36 g; melting point 84°-90° C. with decomposition; $[\alpha]_D^{21} = -35.3°$ (c=1, in methanol).

13f. Pgl-His-Trp-Ser-Tyr-D-Ser(β-Lac)-Leu-Arg-Pro-NH-C$_2$H$_5$-acetate 1.72 g (1 mmol) of H-Trp-Ser-Tyr-D-Ser(Ac$_7$-β-Lac)-Leu-Arg-Pro-NH-C$_2$H$_5$ tosylate are reacted in a similar manner to Example 11h.

Yield as crude acetate: 1.25 g.

Yield after chromatographic purification: 608 mg, $[\alpha]_D^{22} = -33.4°$ (c=1, in water).

EXAMPLE 14

Pgl-His-Trp-Ser-Tyr-D-Ser(β-L-Xyl)-Leu-Arg-Pro-NH-C$_2$H$_5$

14a. Fmoc-D-Ser(β-L-Xyl)-OBzl

Fmoc-D-Ser-OBzl and 2,3,4-tri-O-acetyl-β-L-xylopyranosyl bromide are reacted in a similar manner to Example 8a.

14b. Fmoc-D-Ser(β-L-Xyl)-OH

Fmoc-D-Ser(β-L-Xyl)-OBzl is catalytically hydrogenated in a similar manner to Example 8b.

$[\alpha]_D^{22} = +20.4°$ (c=1, in ethyl acetate).

14c. H-D-Ser(β-L-Xyl)-Leu-Arg-Pro-NH-C$_2$H$_5$-tosylate 4.1 g (7 mmol) of Fmoc-D-Ser(Ac$_3$-β-L-Xyl)-OH are reacted in a similar manner to Example 1d with 5.3 g of H-Leu-Arg-Pro-NH-C$_2$H$_5$ ditosylate.

The foamy residue is reacted and purified in a similar manner to Examples 3d and 4e.

Yield 4.95 g; $[\alpha]_D^{21} = -33.1°$ (c=1, in water).

14d. Fmoc-Trp-Ser-Tyr-D-Ser(Ac$_3$-β-L-Xyl)-Leu-Arg-Pro-NH-C$_2$H$_5$-tosylate 2.8 g (3 mmol) of H-D-Ser(Ac$_3$-β-L-Xyl)-Leu-Arg-Pro-NH-C$_2$H$_5$ are reacted in a similar manner to Example 11f with 2.03 g of Fmoc-Trp-Ser-Tyr.

Yield 4.65 g; melting point 109°-114° C. with decomposition; $[\alpha]_D^{21} = -18.7°$ (c=1, in methanol).

14e. H-Trp-Ser-Tyr-D-Ser(Ac$_3$-β-L-Xyl)-Leu-Arg-Pro-NH-C$_2$H$_5$-tosylate 3.18 g of Fmoc-Trp-Ser-Tyr-D-Ser(Ac$_3$-β-L-Xyl)-Leu-Arg-Pro-NH-C$_2$H$_5$ tosylate are reacted in a similar manner to Example 11g.

Yield 2.75 g; melting point 98°-103° C. with decomposition; $[\alpha]_D^{21} = -20.5°$ (c=1, in methanol).

14f. Pgl-His-Trp-Ser-Tyr-D-Ser(β-L-Xyl)-Leu-Arg-Pro-NH-C$_2$H$_5$-acetate 1.36 g of H-Trp-Ser-Tyr-D-Ser(Ac$_3$-β-L-Xyl)-Leu-Arg-Pro-NH-C$_2$H tosylate are reacted in a similar manner to Example 11h.

Yield as crude acetate: 988 mg.

Yield after chromatographic purification: 278 mg; $[\alpha]_D^{22} = -28.5°$ (c=1, in water).

EXAMPLE 15

Pgl-His-Trp-Ser-Tyr-D-Trp-Ser(L-Ara)-Arg-Pro-NH-$C_2H_5$

15a. Fmoc-Ser($Ac_3$-L-Ara)-OBzl

Fmoc-D-Ser-OBzl and 2,3,4-tri-O-acetyl-L-arabinopyranosyl bromide are reacted in a similar manner to Example 8a.

$[\alpha]_D^{22} = +0°$ (c=1, in chloroform).

15b. Fmoc-Ser($Ac_3$-L-Ara)-OH

Fmoc-Ser($Ac_3$-L-Ara)-OBzl is catalytically hydrogenated in a similar manner to Example 8b.

$8\alpha]_D^{22} = +9.8°$ (c=1, in chloroform).

15c. H-Ser($Ac_3$-L-Ara)-Arg-Pro-NH-$C_2H_5$-tosylate 4.1 g (7 mmol) of Fmoc-Ser($Ac_3$-L-Ara)-OH are reacted in a similar manner to Example 1d with 4.5 g of H-Arg-Pro-NH-$C_2H_5$ ditosylate.

The foamy residue is reacted in a similar manner to Example 6c.

Yield 4.8 g; $[\alpha]_D^{21} = 41.3°$ (c=1, in water).

15d. Fmoc-D-Trp-Ser($Ac_3$-L-Ara)-Arg-Pro-NH-$C_2H_5$-tosylate 4.08 g (5 mmol) of H-Ser($Ac_3$-L-Ara)-Arg-Pro-NH-$C_2H_5$-tosylate are reacted with 2.14 g of Fmoc-D-Trp-OH in a similar manner to Example 6d.

Yield 5.7 g; melting point 95°–97°°C. with decomposition; $[\alpha]_D^{23} = -26.3°$ (c=1, in methanol).

15e. H-D-Trp-Ser($Ac_3$-L-Ara)-Arg-Pro-NH-$C_2H_5$-tosylate 4.88 g (4 mmol) of Fmoc-D-Trp-Ser($Ac_3$-L-Ara)-Arg-Pro-NH-$C_2H_5$ are reacted in a similar manner to Examples 3d and 4c.

Yield 2.23 g; $[\alpha]_D^{23} = -71.8°$ (c=1, in water).

15f. Fmoc-Trp-Ser-Tyr-D-Trp-Ser($Ac_3$-L-Ara)-Arg-Pro-NH-$C_2H_5$-tosylate 2.5 g (2.5 mmol) of H-D-Trp-Ser($Ac_3$-L-Arg)-Arg-Pro-NH-$C_2H_5$ tosylate are reacted in a similar manner to Example 11f with 1.7 g of Fmoc-Trp-Ser-Tyr-OH.

Yield 3.65 g; melting point 147°–149° with decomposition; $[\alpha]_D^{23} = -37.3°$ (c=1, in methanol).

15g. H-Trp-Ser-Tyr-D-Trp-Ser($Ac_3$-L-Ara)-Arg-Pro-NH-$C_2H_5$-tosylate 3.3 g (2 mmol) of Fmoc-Trp-Ser-Tyr-D-Trp-Ser-($Ac_3$-L-Ara)-Arg-Pro-NH-$C_2H_5$ are reacted in a similar manner to Example 11g.

Yield 2.3 g; melting point 92°–94° C. with decomposition; $[\alpha]_D^{23} = -36.6°$ (c=1, in methanol).

15h. Pgl-His-Trp-Ser-Tyr-D-Trp-Ser(L-Ara)-Arg-Pro-NH-$C_2H_5$-acetate 1.4 g (1 mmol) of H-Trp-Ser-Tyr-D-Trp-Ser($Ac_3$-L-Ara)-Arg-Pro-NH-$C_2H_5$ tosylate are reacted in a similar manner to Example 11H with 450 mg Pgl-His(Dnp)-OH.

Yield of crude acetate: 795.2 mg.

Yield after chromatographic purification: 405 mg; $[\alpha]_D^{22} = -39.3°$ (c=1, in water).

EXAMPLE 16

Pgl-His-Trp-Ser-Tyr-D-Trp-Ser($\beta$-L-Xyl)-Arg-Pro-NH-$C_2H_5$

16a. Fmoc-Ser($Ac_3$-$\beta$-L-Xyl)-OBzl

Fmoc-Ser-OBzl and 2,3,4-tri-O-acetyl-$\beta$-L-xylopyranosyl bromide are reacted in a similar manner to Example 8a.

16b. Fmoc-Ser($Ac_3$-$\beta$-L-Xyl)-OH

Fmoc-Ser($Ac_3$-$\beta$-L-Xyl)-OBzl is catalytically hydrogenated in a similar manner to Example 8b.

$[\alpha]_D^{22} = +54.4°$ (c=1, in methanol).

16d. H-Ser($Ac_3$-$\beta$-L-Xyl)-Arg-Pro-NH-$C_2H_5$-tosylate 4.1 g (7 mmol) of Fmoc-Ser($Ac_3$-$\beta$-L-Xyl)-OH are reacted in a similar manner to Example 1d with 4.5 g of H-Arg-Pro-NH-$C_2H_5$ ditosylate.

The foamy residue is reacted in a similar manner to

EXAMPLE 6c

Yield 4.1 g; $[\alpha]_D^{21} = -9.6°$ (c=1, in water).

16d. Fmoc-D-Trp-Ser($Ac_3$-$\beta$-L-Xyl)-Arg-Pro-NH-$C_2H_5$-tosylate 4.08 g (5 mmol) of H-Ser($Ac_3$-$\beta$-L-Xyl)-Arg-Pro-NH-$C_2H_5$ tosylate are reacted in a similar manner to Example 6d with 2.15 g of Fmoc-D-Trp-OH.

Yield 5.7 g; melting point 81°–83° C. with decomposition; $[\alpha]_D^{21} = +1.3°$ (c=1, in methanol).

16e. H-D-Trp-Ser($Ac_3$-$\beta$-L-Xyl)-Arg-Pro-NH-$C_2H_5$-tosylate 4.9 g (4 mmol) of Fmoc-D-Trp-Ser($Ac_3$-$\beta$-L-Xyl)-Arg-Pro-NH-$C_2H_5$ are reacted in a similar manner to Examples 3d and 4c. For purification, the material is shaken with ethyl acetate and freeze-dried.

Yield 2.6 g; $[\alpha]_D^{21} = -42.5°$ (c=1, in water).

16f. Fmoc-Trp-Ser-Tyr-D-Trp-Ser($Ac_3$-$\beta$-L-Xyl)-Arg-Pro-NH-$C_2H_5$-tosylate 2.4 g (2.4 mmol) of H-D-Ser($Ac_3$-$\beta$-L-Xyl)-Arg-Pro-NH-C-$C_2H_5$ tosylate are reacted in a similar manner to Example 11f with 1.63 g of Fmoc-Trp-Ser-Tyr-OH.

Yield 3.95 g; melting point 132°–137° with decomposition; $[\alpha]_D^{21} = -28.9°$ (c=1, in methanol).

16g. H-Trp-Ser-Tyr-D-Trp-Ser($Ac_3$-$\beta$-L-Xyl)-Arg-Pro-NH-$C_2H_5$-tosylate 3.3 g (2 mmol) of Fmoc-Trp-Ser-Tyr-D-Ser($Ac_3$-$\beta$-L-Xyl)-Arg-Pro-NH-$C_2H_5$ tosylate are reacted in a similar manner to Example 11g.

Yield 2.74 g; melting point 131° to 140° C. with decomposition; $[\alpha]_D^{21} = -26.8°$ (c=1, in methanol).

16h. Pgl-His-Trp-Ser-Tyr-D-Trp-Ser($\beta$-L-Xyl)-Arg-Pro-NH-$C_2H_5$-acetate 1.44 g (1 mmol) of H-Trp-Ser-Tyr-D-Trp-Ser($Ac_3$-$\beta$-L-Xyl)-Arg-Pro-NH-$C_2H_5$ tosylate are reacted in a similar manner to Example 11a with 450 mg of Pgl-His(Dnp)-OH.

Yield of crude acetate: 1.14 g.

Yield after chromatographic purification: 533 mg; $[\alpha]_D^{22} = -42.3°$ (c=1, in water).

EXAMPLE 17

Pgl-His-Trp-Ser-Tyr-D-Trp-Ser($\beta$-Lac)-Arg-Pro-NH-$C_2H_5$

17a. Fmoc-Ser($Ac_7$-$\beta$-Lac)-OBzl

Fmoc-Ser-OBzl and 2,3,6,2',3',4',6'-hepta-O-acetyl-lactopyranosyl bromide are reacted in a similar manner to Example 8a.

$[\alpha]_D^{22} = +10.6°$ (c=1, in chloroform).

17b. Fmoc-Ser($Ac_7$-$\beta$-Lac)-OH

Fmoc-Ser($Ac_3$-$\beta$-Lac) is catalytically hydrogenated as in Example 8b.

$[\alpha]_D^{22} = +10.6°$ (c=1, chloroform).

17c. H-Ser($Ac_7$-$\beta$-Lac)-Arg-Pro-NH-$C_2H_5$-tosylate 4.49 g (4.75 mmol) of Fmoc-Ser($Ac_7$-$\beta$-Lac)-OH are reacted in a similar manner to Example 1d with 3.05 g of H-Arg-Pro-NH-$C_2H_5$ ditosylate.

The foamy residue is reacted in a similar manner to Example 6c.

Yield 4.57 g; $[\alpha]_D^{21} = -24.8°$ (c=1, in water).

17d. Fmoc-D-Trp-Ser(Ac$_7$-β-Lac)-Arg-Pro-NH-C$_2$H$_5$-tosylate 3.53 g (3 mmol) of H-Ser(Ac$_7$-β-Lac)-Arg-Pro-NH-C$_2$H$_5$ tosylate are reacted in a similar manner to Example 6d with 1.28 g of Fmoc-D-Trp-OH. Fmoc-D-Trp-OH.

Yield 4.4 g; melting point 106°–109° C. with decomposition; $[\alpha]_D^{21} = -25.1°$ (c=1, in methanol).

17e. H-D-Trp-Ser(Ac$_7$-β-Lac)-Arg-Pro-NH-C$_2$H$_5$-tosylate 3.96 g (2.5 mmol) of Fmoc-D-Trp-Ser(Ac$_7$-β-Lac)-Arg-Pro-NH-C$_2$H$_5$ tosylate are reacted in a similar manner to Examples 3d and 4c.

Yield 2.37 g; $[\alpha]_D^{21} = -54.6°$ (c=1, in water).

17f. Fmoc-Trp-Ser-Tyr-D-Trp-Ser(Ac$_7$-β-Lac)-Arg-Pro-NH-C$_2$H$_5$-tosylate 2.25 g (1.65 mmol) of H-D-Trp-Ser(Ac$_7$-β-Lac)-Arg-Pro-NH-C$_2$H$_5$ tosylate are reacted in a similar manner to Example 11f with 1.12 g of Fmoc-Trp-Ser-Tyr-Oh.

Yield 2.65 g; melting point 109°–111° C. with decomposition; $[\alpha]_D^{21} = -30.0°$ (c=1, in methanol).

17g. H-Trp-Ser-Tyr-D-Trp-Ser((Ac$_7$-β-Lac)-Arg-Pro-NH-C$_2$H$_5$-tosylate 2.43 g (1.2 mmol) of Fmoc-Trp-Ser-Tyr-D-Trp-Ser-(Ac$_7$-β-Lac)-Arg-Pro-NH-C$_2$H$_5$ tosylate are reacted in a similar manner to Example 11g.

Yield 1.93 g; melting point 136°–142° C. with decomposition; $[\alpha]_D^{21} = -33.3°$ (c=1, in methanol).

17h. Pgl-His-Trp-Ser-Tyr-D-Trp-Ser(β-Lac)-Arg-Pro-NH-C$_2$H$_5$-acetate 1.8 g (1 mmol) of H-Trp-Ser-Tyr-D-Trp-Ser(Ac$_7$-β-Lac)-Arg-Pro-NH-C$_2$H$_5$ tosylate are reacted in a similar manner to Example 11h with 450 mg of Pgl-His(Dnp)-OH.

Yield of crude acetate: 1.24 g.

Yield after chromatographic purification: 579 mg; $[\alpha]_D^{22} = -39.6°$ (c=1, in water).

EXAMPLE 18

Pgl-His-Trp-Ser-Tyr-D-Trp-Ser(β-D-Glc-NAc)-Arg-Pro-NH-C$_2$H$_5$

18a. Fmoc-Ser(Ac$_3$-β-D-Glc-NAc)-OBzl

Fmoc-Ser-OBzl and 2-N-acetyl-3,4,6-tri-O-acetyl-glucosaminyl bromide are reacted in a similar manner to Example 8a.

$[\alpha]_D^{22} = -6.6°$ (c=1, in chloroform/methanol 3:1),

18b. Fmoc-Ser(Ac$_3$-β-D-Glc-NAc)-OH

Fmoc-Ser(Ac$_3$-β-D-Glc-NAc)-OBzl is catalytically hydrogenated in a similar manner to Example 8b.

$[\alpha]_D^{22} = 1.6°$ (c=1, in chloroform/methanol 3:1).

18c. H-Ser(Ac$_3$-β-D-Glc-NAc)-Arg-Pro-NH-C$_2$H$_5$-tosylate 3.37 g (5 mmol) of Fmoc-Ser(Ac$_3$-β-D-Glc-NAc)-OH are reacted in a similar manner to Example 1d with 3.21 g of H-Arg-Pro-NH-C$_2$H$_5$ ditosylate.

The foamy residue is reacted in a similar manner to Example 6c.

Yield 4.21 g; $[\alpha]_D^{22} = -47.8°$ (c=1, in water).

18d. Fmoc-D-Trp-Ser(Ac$_3$-β-D-Glc-NAc)-Arg-Pro-NH-C$_2$H$_5$-tosylate 3.61 g (4 mmol) of H-Ser(Ac$_3$-β-D-Glc-NAc)-Arg-Pro-NH-C$_2$H$_5$ tosylate are reacted in a similar manner to Example 6d with 1.71 g of Fmoc-D-Trp-OH.

Yield 4.95 g; melting point 93°–95° C. with decomposition; $[\alpha]_D^{22} = -32.3°$ (c=1, in methanol).

18e. H-D-Trp-Ser(Ac$_3$-β-D-Glc-NAc)-Arg-Pro-NH-C$_2$H$_5$-tosylate 4.49 g (3.5 mmol) of Fmoc-D-Trp-Ser(Ac$_3$-β-D-Glc-NAc)-Arg-Pro-NH-C$_2$H$_5$ tosylate are reacted in a similar manner to Examples 3d and 4c.

Yield 3.68 g; melting point 105°–107° C. with decomposition.

18f. Fmoc-Trp-Ser-Tyr-D-Trp-Ser(Ac$_3$-β-D-Glc-NAc)-Arg-Pro-NH-C$_2$H$_5$-tosylate 3.27 g (3 mmol) of H-D-Trp-Ser(Ac$_3$-β-D-Glc-NAc)-Arg-Pro-NH-C$_2$H$_5$ tosylate are reacted in a similar manner to Example 11f with 2.03 g of Fmoc-Trp-Ser-Tyr-OH.

Yield 4.24 g; melting point 145°–146° with decomposition; $[\alpha]_D^{22} = -17.6°$ (c=1, in methanol).

18g. H-Trp-Ser-Tyr-D-Trp-Ser(Ac$_3$-β-D-Glc-NAc)-Arg-Pro-NH-C$_2$H$_5$-tosylate 3.5 g (2 mmol) of Fmoc-Trp-Ser-Tyr-D-Trp-Ser-(Ac$_3$-β-D-Glc-NAc)-Arg-Pro-NH-C$_2$H$_5$ tosylate are reacted in a similar manner to Example 11g.

Yield 3.05 g; melting point 104°–107° C. with decomposition; $[\alpha]_D^{22} = -16.3°$ (c=1, in methanol).

18h. Pgl-His-Trp-Ser-Tyr-D-Trp-Ser(Ac$_3$-β-D-Glc-NAc)-Arg-Pro-NH-C$_2$H$_5$-tosylate 1.52 g (1 mmol) of H-Trp-Ser-Tyr-D-Trp-Ser(Ac$_3$-β-D-Glc-NAc)-Arg-Pro-NH-C$_2$H$_5$ are reacted in a similar manner to Example 11h with 450 mg of Pgl-His(Dnp)-OH.

Yield as crude acetate: 1.178 g.

Yield after chromatographic purification: 353 mg; $[\alpha]_D^{22} = -50.8°$ (c=1, in water).

EXAMPLE 19

Pgl-His-Trp-Ser-Tyr-D-Trp-Ser(D-Rib)-Arg-Pro-NH-C$_2$H$_5$

19a. Fmoc-Ser(Ac$_3$-D-Rib)-OBzl

Fmoc-Ser-OBzl and 2,3,4-tri-O-acetyl-D-ribopyranosyl bromide are reacted in a similar manner to Example 8a.

$[\alpha]_D^{22} = -51.3°$ (c=1, in chloroform).

19b. Fmoc-Ser(Ac$_3$-D-Rib)-OBzl

Fmoc-Ser(Ac$_3$-D-Rib)-OBzl is catalytically hydrogenated as in Example 8b.

$[\alpha]_D^{22} = -23.8°$ (c=1, in chloroform).

19c. H-Ser(Ac$_3$-D-Rib)-Arg-Pro-NH-C$_2$H$_5$-tosylate 4.1 g (7 mmol) of Fmoc-Ser(Ac$_3$-D-Rib)-OH are reacted in a similar manner to Example 1d with 4.5 g of H-Arg-Pro-NH-C$_2$H$_5$ ditosylate.

The foamy residue is reacted in a similar manner to Example 6c.

Yield 5.45 g; $[\alpha]_D^{22} = -65.7°$ (c=1, in water).

19d. Fmoc-D-Trp-Ser(Ac$_3$-D-Rib)-Arg-Pro-NH-C$_2$H$_5$-tosylate 4.08 g (5 mmol) of H-Ser(Ac$_3$-D-Rib)-Arg-Pro-NH-C$_2$H$_5$-tosylate are reacted in a similar manner to Example 6d with 2.15 g of Fmoc-D-Trp-OH.

Yield 5.74 g; melting point 104°–107° C. with decomposition; $[\alpha]_D^{22} = -40.7°$ (c=1, in methanol).

19e. H-D-Trp-Ser(Ac$_3$-D-Rib)-Arg-Pro-NH-C$_2$H$_5$-tosylate 4.21 g (4 mmol) of Fmoc-D-Trp-Ser(Ac$_3$-D-Rib)-Arg-Pro-NH-C$_2$H$_5$ tosylate are reacted in a similar manner to Example 3d and 4c.

Yield 3.22 g; melting point 98°–101 C.; $[\alpha]_D^{22} = -27.0°$ (c=1, in methanol).

19f. Fmoc-Trp-Ser-Tyr-D-Trp-Ser(Ac$_3$-D-Rib)-Arg-Pro-NH-C$_2$H$_5$-tosylate 3.01 g (3 mmol) of H-D-Trp-Ser(Ac$_3$-D-Rib)-Arg-Pro-NH-C$_2$H$_5$ tosylate are reacted in a similar manner to Example 11f with 2.03 g of Fmoc-Trp-Ser-Tyr-OH.

Yield 4.63 g; melting point 147°-149° C. with decomposition; $[\alpha]_D^{22}=-25.6°$ (c=1, in methanol).

19g. H-Trp-Ser-Tyr-D-Ser(Ac$_3$-D-Rib)-Arg-Pro-NH-C$_2$H$_5$-tosylate 4.15 g (2.5 mmol) of Fmoc-Trp-Ser-Tyr-D-Trp-Ser-(Ac$_3$-D-Rib)-Arg-Pro-NH-C$_2$H$_5$ tosylate are reacted in a similar manner to Example 11g.

Yield 3.75 g; melting point 99°-102 C. with decomposition; $[\alpha]_D^{22}=-27.2°$ (c=1, in methanol).

19H. Pgl-His-Trp-Ser-Tyr-D-Trp-Ser(D-Rib)-Arg-Pro-NH-C$_2$H$_5$-acetate 1.44 g (1 mmol) of H-Trp-Ser-Tyr-D-Trp-Ser(Ac$_3$-D-Rib)-Arg-Pro-NH-C$_2$H$_5$tosylate are reacted in a similar manner to Example 11h with 450 mg of Pgl-His(Dnp)-OH.

Yield of crude acetate: 975.8 mg; yield after purification: 495 mg; $[\alpha]_D^{22}=-60.6°$ (c=1, in water).

EXAMPLE 20

Pgl-His-Trp-Ser-Tyr-D-Trp-Ser(D-Ara)-Arg-Pro-NH-C$_2$H$_5$

20a. Fmoc-Ser(Ac$_3$-D-Ara)-OBzl

Fmoc-Ser-OBzl and 2,3,4-tri-O-acetyl-D-arabinopyranosyl bromide are reacted in a similar manner to Example 8a.

$[\alpha]_D^{22}=+8.9°$ (c=1, in chloroform).

20b. Fmoc-Ser(Ac$_3$-D-Ara)-OH

Fmoc-Ser(Ac$_3$-D-Ara)-OBzl is catalytically hydrogenated in a similar manner to Example 8b.

$[\alpha]_D^{22}=+20.8°$ (c=1, in chloroform).

20c. H-Ser(Ac$_3$-D-Ara)-Arg-Pro-NH-C$_2$H$_5$-tosylate 4.1 g (7 mmol) of Fmoc-Ser(Ac$_3$-D-Ara)-OH are reacted in a similar manner to Example 1d with 4.5 g of H-Arg-Pro-NH-C$_2$H$_5$ ditosylate.

The foamy residue is reacted in a similar manner to Example 6c.

Yield 2.95 g; $[\alpha]_D^{22}=-29°$ (c=1, in water).

20d. Fmoc-D-Trp-Ser(Ac$_3$-D-Ara)-Arg-Pro-NH-C$_2$H$_5$-tosylate 2.45 g (3 mmol) of H-Ser(Ac$_3$-D-Ara)-Arg-Pro-NH-C$_2$H$_5$-tosylate are reacted in a similar manner to Example 6d with 1.28 g of Fmoc-D-Trp-OH.

Yield 3.22 g; melting point 101°-103° C. with decomposition; $[\alpha]_D^{22}=-21.8°$ (c=1, in methanol).

20e. H-D-Trp-Ser(Ac$_3$-D-Ara)-Arg-Pro-NH-C$_2$H$_5$-tosylate 2.63 g (2.5 mmol) of Fmoc-D-Trp-Ser(Ac$_3$-D-Ara)-Arg-Pro-NH-C$_2$H$_5$ tosylate are reacted in a similar manner to Examples 3d and 4c.

Yield 2.19 g; melting point 102°-105° C. with decomposition; $[\alpha]_D^{22}=-14.3°$ (c=1, in methanol)

20f. Fmoc-Trp-Ser-Tyr-D-Trp-Ser(Ac$_3$-D-Ara)-Arg-Pro-NH-C$_2$H$_5$-tosylate 2.0 g (2 mmol) of H-D-Trp-Ser(Ac$_3$-D-Ara)-Arg-Pro-NH-C$_2$H$_5$ tosylate are reacted in a similar manner to Example 11f with 1.35 g of Fmoc-Trp-Ser-Tyr-OH.

Yield 2.77 g; melting point 150°-151° with decomposition; $[\alpha]_D^{22}=-16.0°$ (c=1, in methanol).

20g. H-Trp-Ser-Try-D-Trp-Ser(Ac$_3$-D-Ara)-Arg-Pro-NH-C$_2$H$_5$-tosylate 2.45 g (1.5 mmol) of Fmoc-Trp-Ser-Tyr-D-Trp-Ser-(Ac$_3$-D-Ara)-Arg-Pro-NH-C$_2$H$_5$ tosylate are reacted in a similar manner to Example 11g.

Yield 2.1 g; melting point 109°-110° with decomposition; $[\alpha]_D^{22}=-29.4°$ (c=1, in methanol).

20h. Pgl-His-Trp-Ser-Tyr-D-Trp-Ser(Ac$_3$-D-Ara)-Arg-Pro-NH-C$_2$H$_5$-acetate 1.44 g (1 mmol) of H-Trp-Ser-Tyr-D-Trp-Ser(Ac$_3$-D-Ara)-Arg-Pro-NH-C$_2$H$_5$ tosylate are reacted in a similar manner to Example 11h with 450 mg of Pgl-His(Dnp)-OH.

Yield of crude acetate: 1.033 g

Yield after chromatographic purification: 336 mg; $[\alpha]_D^{22}=-51.7°$ (c=1, in water).

EXAMPLE 21

Pgl-His-Trp-Ser-Tyr-D-Ser(D-Rib)-Leu-Arg-Pro-NH-C$_2$H$_5$

21a. Fmoc-D-Ser(Ac$_3$-D-Rib)-OBzl

Fmoc-D-Ser-OBzl and 2,3,4-tri-O-acetyl-D-ribopyranosyl bromide are reacted in a similar manner to Example 8a.

$[\alpha]_D^{22}=-37.7°$ (c=1, in chloroform).

21b. Fmoc-D-Ser(Ac$_3$-D-Rib)-OH

Fmoc-D-Ser(Ac$_3$-D-Rib)-OBzl is catalytically hydrogenated in a similar manner to Example 8b.

$[\alpha]_D^{22}=-78.9°$ (c=1, in chloroform).

21c. H-D-Ser(Ac$_3$-D-Rib)-Leu-Arg-Pro-NH-C$_2$H$_5$-tosylate 4.1 g (7 mmol) of Fmoc-D-Ser(Ac$_3$-D-Rib)-OH are reacted in a similar manner to Example 1d with 5.3 g of H-Leu-Arg-Pro-NH-C$_2$H$_5$ ditosylate.

The foamy residue is reacted and purified in a similar manner to Examples 3d and 4e.

Yield 6.26 g; $[\alpha]_D^{22}=-79.0°$ (c=1, in water).

21d. Fmoc-Trp-Ser-Tyr-D-Ser(Ac$_3$-D-Rib)-Leu-Arg-Pro-NH-C$_2$H$_5$-tosylate 2.79 g (3 mmol) of H-D-Ser(Ac$_3$-D-Rib)-Leu-Arg-Pro-NH-C$_2$H$_5$ tosylate are reacted in a similar manner to Example 11f with 2.03 g of Fmoc-Trp-Ser-Tyr-OH.

Yield 4.22 g; melting point 144°-146° C. with decomposition; $[\alpha]_D^{22}=-44.1°$ (c=1, in methanol).

21e. H-Trp-Ser-Tyr-D-Ser(Ac$_3$-D-Rib)-Leu-Arg-Pro-NH-C$_2$H$_5$-tosylate 3.18 g (2 mmol) of Fmoc-Trp-Ser-Tyr-D-Ser(Ac$_3$-D-Rib)-Leu-Arg-Pro-NH-C$_2$H$_5$ tosylate are reacted in a similar manner to Example 11g.

Yield 2.47 g; melting point 136°-138° C. with decomposition; $[\alpha]_D^{22}=-50.9°$ C. (c=1, in methanol).

21f. Pgl-His-Trp-Ser-Tyr-D-Ser(D-Rib)-Leu-Arg-Pro-NH-C$_2$H$_5$-acetate 1.19 g (1 mmol) of H-Trp-Ser-Tyr-D-Ser(Ac$_3$-D-Rib)-Leu-Arg-Pro-NH-C$_2$H$_5$ tosylate are reacted in a similar manner to Example 11h with 450 mg of Pgl-His(Dnp)-OH.

Yield of crude acetate: 734.5 mg.

Yield after chromatographic purification: 349 mg; $[\alpha]_D^{22}=-51.9°$ (c=1, in water).

EXAMPLE 22

Pgl-His-Trp-Ser-Tyr-D-Ser(D-Ara)-Leu-Arg-Pro-NH-C$_2$H$_5$

22a. Fmoc-D-Ser(Ac$_3$-D-Ara)-OBzl

Fmoc-D-Ser-OBzl and 2,4,5-triacetylarabinopyranosyl bromide are reacted in a similar manner to Example 8a.

$[\alpha]_D^{22} = -0.5°$ (c=1, in chloroform).

22b. Fmoc-D-Ser(Ac₃-D-Ara)-OH

Fmoc-D-Ser(Ac₃-D-Ara)-OBzl is catalytically hydrogenated in a similar manner to Example 8b.

$[\alpha]_D^{22} = -5.8°$ (c=1, in chloroform).

22c. H-D-Ser(Ac₃-D-Ara)-Leu-Arg-Pro-NH-C₂H₅-tosylate 3.51 g (5 mmol) of Fmoc-D-Ser(Ac₃-D-Ara)-OH are reacted in a similar manner to Example 1d with 4.54 g of H-Leu-Arg-Pro-NH-C₂H₅ ditosylate.

The foamy residue is reacted and purified in a similar manner to Examples 3d and 4e.

Yield 5.47 g; $[\alpha]_D^{22} = -47.8°$ (c=1, in water).

22d. Fmoc-Trp-Ser-Tyr-D-Ser(Ac₃-D-Ara)-Leu-Arg-Pro-NH-C₂H₅-tosylate 2.79 g (3 mmol) of H-D-Ser(Ac₃-D-Ara)-Leu-Arg-Pro-NH-C₂H₅ tosylate are reacted in a similar manner to Example 11f with 2.03 g of Fmoc-Trp-Ser-Tyr-OH.

Yield 4.18 g; melting point 152°-154° C. decomposition; $[\alpha]_D^{22} = -30.4°$ (c=1, in methanol).

22e. H-Trp-Ser-Tyr-D-Ser(Ac₃-D-Ara)-Leu-Arg-Pro-NH-C₂H₅-tosylate 3.18 g (2 mmol) of Fmoc-Trp-Ser-Tyr-D-Ser(Ac₃-D-Ara)-Leu-Arg-Pro-NH-C₂H₅ tosylate are reacted in a similar manner to Example 11g.

Yield 2.62 g; melting point 101°-104° C. with decomposition; $[\alpha]_D^{22} = -31.6°$ (c=1, in methanol).

22f. Pgl-His-Trp-Ser-Tyr-D-Ser(D-Ser(D-Ara)-Leu-Arg-Pro-NH-C₂H₅-acetate 1.19 g of H-Trp-Ser-Tyr-D-Ser(Ac₃-D-Ara)-Leu-Arg-Pro-NH-C₂H₅ tosylate are reacted in a similar manner to Example 11h with 450 mg of Pgl-His(Dnp)-OH.

Yield of crude acetate: 778.3 mg.

Yield after chromatographic purification: 365 mg; $[\alpha]_D^{22} = -32.6°$ (c=1, in water).

EXAMPLE 23

Pgl-His-Trp-Ser-Tyr-D-Ser(β-D-Glc-NAc)-Leu-Arg-Pro-NH-C₂H₅

23a. Fmoc-D-Ser(Ac₃-β-D-Glc-NAc)-OBzl

Fmoc-D-Ser-OBzl and N-acetyl-3,4,6-tri-O-acetyl-glucosaminopyranosyl bromide are reacted in a similar manner to Example 8a.

$[\alpha]_D^{22} = -11.0°$ (c=1, in ethyl acetate).

23b. Fmoc-D-Ser(Ac₃-β-D-Glc-NAc)-OH

Fmoc-D-Ser(Ac₃-β-D-Glc-NAc)-OBzl is catalytically hydrogenated in a similar manner to Example 8b.

$[\alpha]_D^{22} = -23.8°$ (c=1, in ethyl acetate).

23c. H-D-Ser(Ac₃-β-D-Glc-NAc)-Leu-Arg-Pro-NH-C₂H₅-tosylate 3.37 g (5 mmol) of Fmoc-D-Ser(Ac₃-β-D-Glc-NAc)-OH are reacted in a similar manner to Example 1d with 3.75 g of H-Leu-Arg-Pro-NH-C₂H₅ ditosylate.

The foamy residue is reacted in a similar manner to Example 6c.

Yield 3.96 g; $[\alpha]_D^{22} = -69.4°$ (c=1, in water).

23d. Fmoc-Trp-Ser-Tyr-D-Ser(Ac₃-β-D-Glc-NAc)-Leu-Arg-Pro-NH-C₂H₅-tosylate 3.05 g (3 mmol) of H-D-Ser(Ac₃-β-Glc-NAc)-Leu-Arg-Pro-NH-C₂H₅ tosylate are reacted in a similar manner to Example 11f with 2.03 g of Fmoc-Trp-Ser-Tyr-OH.

Yield 4.34 g; melting point 139°-144° C. with decomposition; $[\alpha]_D^{22} = -36.8°$ (c=1, methanol).

23e. H-Trp-Ser-Tyr-D-Ser(Ac₃-β-Glc-NAc)-Leu-Arg-Pro-NH-C₂H₅-tosylate 3.35 g (2 mmol) of Fmoc-Trp-Ser-Tyr-D-Ser(Ac₃-β-D-Glc-NAc)-Leu-Arg-Pro-NH-C₂H₅ tosylate are reacted in a similar manner to Example 11f with 2.03 g of Fmoc-Trp-Ser-Tyr-OH.

Yield 4.34 g; melting point 139°-144° C. with decomposition; $[\alpha]_D^{22} = -36.8°$ (c=1, in methanol).

23e. H-Trp-Ser-Tyr-D-Ser(Ac₃-β-Glc-NAc)-Leu-Arg-Pro-NH-C₂H₅-tosylate 3.35 g (2 mmol) of Fmoc-Trp-Ser-Tyr-D-Ser(Ac₃-β-D-Glc-NAc)-Leu-Arg-Pro-NH-C₂H₅ tosylate are reacted in a similar manner to Example 11g.

Yield 2.3 g; melting point 123°-127° C. with decomposition; $[\alpha]_D^{22} = -40.2°$ (c=1, in methanol).

23f. Pgl-His-Trp-Ser-Tyr-D-Ser(β-D-Glc-NAc)-Leu-Arg-Pro-NH-C₂H₅-acetate 1.45 g (1 mmol) of H-Trp-Ser-Tyr-D-Ser(Ac₃-β-Glc-NAc)-Leu-Arg-Pro-NH-C₂H₅ tosylate are reacted in a similar manner to Example 11h with 450 mg of Pgl-His(Dnp)-OH.

Yield of crude acetate: 950 mg.

Yield after chromatographic purification: 353 mg; $[\alpha]_D^{22} = -53.1°$ (c=1, in water).

EXAMPLE 24

Ac-D-Nal-p-Cl-D-Phe-D-Trp-Ser-Tyr-D-Ser(α-L-Rha)-Leu-Arg-Pro-Azagly-NH₂

24a. Fmoc-D-Trp-Ser(tBu)-OtBu

To a solution ob 17.1 g (40 mmol) of Fmoc-D-Trp-OH, 10.12 g of H-Ser(tBu)-OtBu.HCl and 5.4 g of HOBt in 100 ml of dimethylformamide, 5.2 ml of N-ethylmorpholine are added at 0° C. with stirring, followed by 8.8 g of DCC. After allowing to stir for 1 hour at 0° C. and 3 hours at room temperature, the precipitate is filtered off with suction and the filtrate is concentrated in vacuo. The residue is dissolved in ethyl acetate and washed successively with water, saturated NaHCO₃ solution and water, dried over Na₂SO₄ and concentrated in vacuo. The solution of the resulting oil in 70 ml of diethyl ether is dropper with stirring into 700 ml of petroleum ether. The precipitate is filtered off with suction and dried.

Yield 17.6 g; melting point 87°-91° C; $[\alpha]_D^{22} = +22.3°$ (c=1, in methanol).

24b. Fmoc-p-Cl-D-Phe-D-Trp-Ser(tBu)-OtBu

To a solution of 16.5 g (26.3 mmol) of Fmoc-D-Trp-Ser(tBu)-OtBu in 150 ml of dimethylformamide, 27.5 ml of diethylamine are added at room temperature and the mixture is allowed to stand 45 minutes at room temperature. The solvent is then distilled off in vacuo and the residue is chromatographed on silica gel first in methylene chloride and thereafter in a mixture of methylene chloride/methanol 9:1.

Yield 7.95 g of H-D-Trp-Ser(tBu)-OtBu.

To a solution of the oil obtained above (19.7 mmol), 8.2 g of Fmoc-p-Cl-D-Phe-Oh and 2.6 g of HOBt in 100 ml of dimethylformamide, 4.3 g of DCC are added. The mixture is worked up as in Example 24a. The residue crystallizes from diethyl ether.

Yield 10.2 g; melting point 184°-186°; $[\alpha]_D^{23} = +14.8°$ (c=1, in methanol).

24c. Ac-D-Nal-p-Cl-D-Phe-D-Trp-Ser(tBu)-OtBu

To a solution of 10 g (12.38 mmol) of Fmoc-p-Cl-D-Phe-D-Trp-Ser(tBu)-OtBu in 100 ml of dimethylformamide, 24.6 ml of diethylamine, are added and the mixture is allowed to stand 20 minutes at room temperature. After distilling off the solvent, the residue is chromatographed on silica gel in methylene chloride.

Yield 7.2 g of an oil.

To a solution of the oil obtained above (12.3 mmol), 2.94 g of Ac-D-Nal-OH and 2.04 g of HOObt in 90 ml of dimethylformamide, 2.7 g of DCC are added at 0° C. The mixture is worked up as in Example 24a. The residue is triturated with diethyl ether, filtered off with suction, dissolved in 18 ml of warm methanol and precipitated with 230 ml of diethyl ether. The precipitate is filtered off with suction after cooling and dried.

Yield 6.4 g; melting point 204°–207° C.; $[\alpha]_D^{22} = -20.5°$ (c=1, in 80% acetic acid).

24d. Ac-D-Nal-P-Cl-D-Phe-D-Trp-Ser-OH

To a solution of 60 ml of 90% aqueous trifluoroacetic acid and 15 ml of 1,2-ethanedithiol, 6.2 g of Ac-D-Nal-p-Cl-D-Phe-D-Trp-Ser(tBu)-OtBu are added at room temperature with stirring. After allowing to stand 75 minutes at room temperature and concentrating in vacuo, the residue is triturated with water, filtered off with suction and dried over $P_2O_5$. The substance is reprecipitated from isopropanol/petroleum ether.

Yield 4.21 g; melting point 195°–197° C.; $[\alpha]_D^{22} = -11.5°$ (c=1, in 80% acetic acid).

24e. Z-Pro-Azagly-NH$_2$

To a solution of 125 g (500 mmol) of Z-Pro-OH, 55 g of semicarbazide hydrochloride and 67.5 g of HOBt in 1000 ml of dimethylformamide, 75 ml of triethylamine and 105 g of DCC are added at 0° C. with stirring. After allowing the react for about a day at 4° C. and filtering off the precipitate with suction, the filtrate is concentrated and the residue is triturated with saturated NaHCO$_3$ solution. The precipitate is filtered off with suction, washed well with water and dried over $P_2O_5$ in vacuo.

Yield 135.3 g; melting point 189° C.

24f. Z-Arg(Z$_2$)-Pro-Azagly-NH$_2$ 131.6 g (430 mmol) of Z-Pro-Azagly-NH$_2$ are catalytically hydrogenated in 1000 ml of a mixture of methanol and dimethylformamide (1:1) in a similar manner to Example 1e. The residue is stirred with water. Insoluble material is filtered off with suction and discarded. The filtrate is concentrated.

Yield 85.2 g of H-Pro-Azagly-NH$_2$.HCl.

To a solution of 20.8 g (100 mmol) of the substance obtained above, 57.6 g of Z-Arg(Z$_2$)-OH and 16.3 g of HOObt in 400 ml of dimethylformamide, 21 g of DCC are added with stirring at 0° C. After working up in a similar manner to Example 24a, the residue is triturated with diethyl ether, decanted off and triturated again with petroleum ether.

Yield 73.4 g; $[\alpha]_D^{20} = -28.4°$ (c=1, in methanol).

24g. H-Arg-Pro-Azagly-NH$_2$.2HCl 37.5 g of Z-Arg-(Z$_2$)-Pro-Azagly-NH$_2$ are catalytically hydrogenated in a similar manner to Example 1e in 350 ml of methanol. The residue is triturated with diethyl ether, filtered off with suction and dried.

Yield 21.95 g; $[\alpha]_D^{21} = -11.4°$ (c=1, in methanol).

24h. H-Leu-Arg-Pro-Azagly-NH$_2$.2HCl 13.2 g (30 mmol) of H-Arg-Pro-Azagly-NH$_2$.2HCl are reacted in a similar manner to Example 1d with 7.92 g of Z-Leu-OH.

Yield 16.7 g of Z-Leu-Arg-Pro-Azagly-NH$_2$.HCl; $[\alpha]_D^{22} = -45.8°$ (c=1, in 80% acetic acid).

14.5 g of the substance obtained above are catalytically hydrogenated in a similar manner to Example 1e in 150 ml of methanol. The residue is triturated with diethyl ether.

Yield 12.35 g; $[\alpha]_D^{22} = -26.4°$ (c=1, in methanol).

24i. Fmoc-D-Ser(Ac$_3$-α-L-Rha)-Leu-Arg-Pro-Azagly-NH$_2$.HCl 10.43 g (17.4 mmol) of Fmoc-D-Ser(Ac$_3$-α-L-Rha)-OH are reacted in a similar manner to Example 1d with 8.95 g of H-Leu-Arg-Pro-Azagly-NH$_2$.2Hcl.

Yield 15.07 g; $[\alpha]_D^{21} = -48.4°$ (c=1, in water).

24k. H-D-Ser(Ac$_3$-α-L-Rha)-Leu-Arg-Pro-Azagly-NH$_2$.HCl

To a solution of 14.3 g (13.5 mmol) of Fmoc-D-Ser-(Ac$_3$-α-L-Rha)-Leu-Arg-Pro-Azagly-NH$_2$.HCl in 65 ml of dimethylformamide, 14.3 ml (135 mmol) of diethylamine are added and the mixture is stirred 10 minutes at room temperature. Thereafter it is concentrated in vacuo and the residue stirred with diethyl ether.

Yield 12.8 g.

For purification, the substance is stirred with 1000 ml of water, filtered off with suction from insoluble material and the filtrate is freeze-dried.

Yield 10.75 g; $[\alpha]_D^{22} = -67.4°$ (c=1, in methanol).

24l. Fmoc-Tyr-D-Ser(Ac$_3$-α-L-Rha)-Leu-Arg-Pro-Azagly-NH$_2$.HCl 3.35 g (4 mmol) of H-D-Ser(Ac$_3$-α-L-Rha)-Leu-Arg-Pro-Azagly-NH$_2$.HCl are reacted in a similar manner to Example 11f with 1.62 g of Fmoc-Tyr-OH. The pentanol phase is next shaken with NaHCO$_3$ solution, then adjusted to pH 7 with 1 N HCl and concentrated. The residue is triturated with diethyl ether.

Yield 4.2 g; $[\alpha]_D^{22} = -35.0°$ (c=1, in methanol).

24m. H-Tyr-D-Ser(Ac$_3$-α-L-Rha)-Leu-Arg-Pro-Azagly-NH$_2$.HCl 3.67 g (3 mmol) of Fmoc-Tyr-D-Ser(Ac$_3$-α-L-Rha)-Leu-Arg-Pro-Azagly-NH$_2$ are reacted in a similar manner to Example 24k. For purification it is partitioned in 3 steps between n-pentanol and water. The aqueous phases and the 2nd and 3rd n-pentanol phases are combined and concentrated, and the residue is triturated with diethyl ether.

Yield 2.3 g; $[\alpha]_D^{21} = -53.2°$ (c=1, in methanol). 24n. Ac-D-Nal-p-Cl-D-Phe-D-Trp-Ser-Tyr-D-Ser(α-L-Rha)-Leu-Arg-Pro-Azagly-NH$_2$-acetate 712 mg (1 mmol) of Ac-D-Nal-p-Cl-D-Phe-D-Trp-Ser-OH are reacted in a similar manner to Example 11h with 1 g of H-Tyr-D-Ser(Ac$_3$-α-L-Rha)-Leu-Arg-Pro-Azagly-NH$_2$.HCl.

Yield of crude acetate: 897 mg.

Yield after chromatographic purification: 214 mg; $[\alpha]_D^{23} = +232.9°$ (c=1, in water).

EXAMPLE 25

Ac-D-Nal-p-Cl-D-Phe-D-Trp-Ser-His-D-Ser(α-L-Rha)-Leu-Arg-Pro-Azagly-NH$_2$

25a. Fmoc-His(Dnp)-D-Ser(Ac$_3$-α-L-Rha)-Leu-Arg-Pro-Azagly-NH$_2$.HCl 3.35 g (4 mmol) of H-D-Ser(Ac$_3$-αL-Rha)-Leu-Arg-Pro-Azagly-NH$_2$.HCl are reacted in a similar manner to Example 24l with 2.17 g of Fmoc-His(Dnp)-OH.

Yield 4.9 g; $[\alpha]_D^{22} = -31.9°$ (c=1, in methanol).

25b. H-His-D-Ser(α-L-Rha)-Leu-Arg-Pro-Azagly-NH$_2$.HCl

To a solution of 4.1 g of Fmoc-His(Dnp)-D-Ser(Ac$_3$-α-L-Rha)-Leu-Arg-Pro-Azagly-NH$_2$.HCl in 15 ml of dimethylacetamide, 3 ml of 100% hydrazine hydrate are added and the mixture is stirred 4 hours at rom temperature. Thereafter it is concentrated in vacuo and the residue is stirred with diethyl ether and filtered off with suction. Thereafter the substance is dissolved in a little methanol, filtered from insoluble material and precipitated with ethyl acetate.

Yield 2.25 g, $[\alpha]_D^{22} = -57.4°$ (c=1, in methanol).

25c. Ac-D-Nal-p-Cl-D-Phe-D-Trp-Ser-His-D-Ser(α-L-Rha)-Leu-Arg-Pro-Azagly-NH₂-acetate 712 mg (1 mmol) of Ac-D-Nal-p-Cl-D-Phe-Trp-Ser-OH are reacted in a similar manner to Example 3e with 850 mg of H-His-D-Ser(α-L-Rha)-Leu-Arg-Pro-Azagly-NH₂.HCl. The residue is triturated with ethyl acetate and dissolved in about 100-150 ml of 30% acetic acid. Insoluble material is filtered off and the filtrate is chromatographed over a weakly basic ion exchanger in the acetate form.

Yield of crude acetate: 1.4 g.

Yield after chromatographic purification: 538 mg; $[\alpha]_D^{24} = -213.1$ (c=1, in water).

EXAMPLE 26

Ac-D-Nal-p-Cl-D-Phe-Trp-Ser-Arg-D-Ser(α-L-Rha)-Leu-Arg-Pro-Azagly-NH₂

26a. Fmoc-Arg-D-Ser(Ac₃-α-L-Rha)-Leu-Arg-Pro-Azagly-NH₂.2HCl

To a solution of 1.59 g (4 mmol) of Fmoc-Arg-OH, 3.35 g of H-D-Ser(Ac₃-α-L-Rha)-Leu-Arg-Pro-Azagly-NH₂.HCl, 540 mg of HOBt and 720 mg of pyridinium perchlorate in 20 ml of dimethylformamide, 880 mg of DCC are added at 0° C. with stirring. After stirring for 1 hour at 0° C. and 3 hours at room temperature, the residue is allowed to stand overnight and the precipitate is filtered off with suction. The filtrate is concentrated in vacuo and the residue is partitioned between n-pentanol and NaHCO₃. The pentanol phase is extracted once again with NaHCO₃ solution and water, adjusted to pH 7 with 1N HCl and concentrated. The residue is triturated with diethyl ether and filtered off with suction.

Yield 4.3 g; $[\alpha]_D^{22} = -37.1°$ (c=1, in methanol).

26b. H-Arg-D-Ser(Ac₃-α-L-Rha)-Leu-Arg-Pro-Azagly-NH₂.2HCl 3.77 g (3 mmol) of Fmoc-Arg-D-Ser(Ac₃-α-L-Rha)-Leu-Arg-Pro-Azagly-NH₂.2HCl are reacted in a similar manner to Example 24k. The product is purified by a 3-stage countercurrent extraction between n-pentanol and water. The 1st and 2nd water phases are combined and freeze-dried.

Yield 2.4 g; $[\alpha]_D^{21} = -28.2°$ (c=1, in methanol)

26c. Ac-D-Nal-p-Cl-D-Phe-D-Trp-Ser-Arg-D-Ser-(α-L-Rha)-Leu Arg-Pro-Azagly-NH₂-diacetate 712 mg (1 mmol) of Ac-D-Nal-p-Cl-D-Phe-D-Trp-Ser-OH are reacted in a similar manner to Example 11h with 1.03 g of H-Arg-D-Ser-(Ac₃-α-L-Rha)-Leu-Arg-Pro-Azagly-NH₂.2HCl.

Yield of crude acetate: 1.06 g.

Yield after chromatographic purification: 550 mg. $[\alpha]_D^{23} = -60.8°$ (c=1, in water).

We claim:

1. A peptide of the formula I

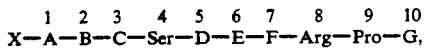

in which

X is hydrogen or (C₁-C₇)-acyl or, if A represents pyroglutamyl, is absent;

A is Pgl, dehydro-Pro, Pro, D-Thi, D-Pgl or D-Nal(2) optionally substituted in the aromatic ring by one or two identical or different radicals from the series bromo, chloro, fluoro, nitro, amino, methyl and methyoxy, D-Phe substituted in this way or D-Trp substituted in this way;

B in His or D-Phe optionally substituted in the phenyl ring by one or two identical or different radicals from the series bromo, chloro, fluoro, nitro, amino, methyl and methoxy;

C is Trp, D-Thi-D-Pal(3) or D-Trp optionally substituted in position 5 and/or 6 by one or two identical or different radicals from the series bromo, chloro, fluoro, nitro, amino, methyl or methoxy;

D is Tyr, Arg or His;

E is D-Ser(R¹), β-Asn, β-Asp-Ome, D-Thi or the radical of A D-Amino acid of general formula II;

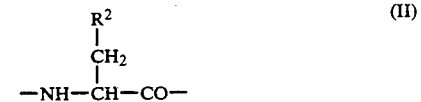

F is Ser(R¹), Leu, Trp or Phe;

G is Gly-NH₂, Aza-Gly-NH₂, D-Ala-NH₂ or NH-(C₁-C₄)-alkyl;

R¹ is optionally partly protected glycosyl radical with at least one free hydroxyl group and R² is hydrogen, (C₁-C₄)-alkoxycarbonyl, (C₁-C₄)-alkoxy, (C₁-C₄)-alkyl which is optionally monosubstituted by (C₁-C₄)-alkoxycarbonyl or (C₁-C₄)alkoxycarbonylamino, phenyl which is optionally substituted by up to three identical or different radicals from the series chloro, fluoro, methyl and (C₁-C₄)-alkoxy, naphthyl, 4, 5,6,7-tetrahydrobenzimidazol-2-yl or indolyl, or a physiologically acceptable salt thereof, with the proviso that a) if E represents a residue of the formula II, β-Asn, β-Asp-OMe or D-Thi, F is exclusively Ser(R¹) and b) if F represents Leu, Phe or Trp, E is exclusively D-Ser(R¹).

2. A peptide of the formula I as claimed in claim 1, wherein

X is absent;
A is Pgl;
B is His;
C is Trp;
D is Tyr or His;
E is D-Ser(R¹), β-Asn, β-Asp-Ome or the residue of a D-amino acid of the formula II;
F is Ser(R¹), Trp or Leu and
G is Gly-NH₂, Aza-Gly-NH₂ or NH-(C₁-C₄)-alkyl and
R¹ and R² are defined in claim 1, or a physiological acceptable salt thereof.

3. A peptide of the formula I as claimed in claim 1, wherein

X is hydrogen or (C₁-C₇)-acyl or is absent,
A is dehydro-Pro, Pro, D-Thi, D-Pgl, optionally substituted D-Nal(2), optionally substituted D-Phe or optionally substituted D-Trp;
B is optionally substituted D-Phe;
C is optionally substituted D-Trp, D-Thi or D-Pal(3);
D is Tyr, Arg or His;
E is D-Ser(R¹), D-Thi or the radical of the D-amino acid of the formula II;
F is Ser(R¹), Leu, Phe or Trp and
G is Gly-NH₂, D-Ala-NH₂, Aza-Gly-NH₂ or NH-(C₁-C₄)-alkyl and
R¹ and R² are as defined in claim 1;

or a physiologically acceptable salt thereof.

4. A peptide of the formula I as claimed in claim 3, wherein
X is $(C_1-C_7)$-acyl,
A is D-Nal(2);
B is D-Phe(Cl);
C is D-Trp;
D is Tyr, His or Arg;
E is D-Ser($R^1$);
F is Ser($R^1$), Leu, Phe or Trp and
G is D-Ala-$NH_2$ or Aza-Gly-$NH_2$ and
$R^1$ and $R^2$ are as defined in claim 1,
or a physiologically acceptable salt thereof.

5. A peptide of the formula I as claimed in claim 1, wherein $R^1$ represents an unprotected glycosyl radical, or a physiologically acceptable salt thereof.

6. A method for the treatment of fertility, which comprises the administration of an effective amount of a peptide as claimed in claim 1 or a physiologically acceptable salt thereof.

7. A method for the treatment of diseases dependent upon gonadotropin, testosterone and estrogen, which comprises the administration of an effective amount of a peptide as claimed in claim 1 or a physiologically acceptable salt thereof.

8. A method for the treatment of steroid-dependent diseases, which comprises the administration of an effective amount of a peptide as claimed in claim 1 or a physiologically acceptable salt thereof.

9. A pharmaceutical composition for the treatment of fertility, comprising an effective amount of a peptide as claimed in claim 1 or a physiologically acceptable salt thereof and a pharmaceutically acceptable carrier.

10. A pharmaceutical composition for the treatment of diseases dependent on gonadotropin, testosterone and estrogen, comprising an effective amount of a peptide as claimed in claim 1 or a physiologically acceptable salt thereof and a pharmaceutically acceptable carrier.

11. A pharmaceutical composition for the treatment of steroid-dependent diseases, comprising an effective amount of a peptide as claimed in claim 1 or a physiologically acceptable salt thereof and a pharmaceutically acceptable carrier.

* * * * *

UNITED STATES PATENT AND TRADEMARK OFFICE
CERTIFICATE OF CORRECTION

PATENT NO. : 5,091,367

DATED : February 25, 1992

INVENTOR(S) : Wolfgang KONIG et al.

It is certified that error appears in the above-identified patent and that said Letters Patent is hereby corrected as shown below:

Abstract, line 7, after "Arg" change "of" to --or--.

Claim 1, column 36, line 1, change "methyoxy" to --methoxy--.

Claim 1, column 36, line 3, after "B" change "in" to --is--.

Claim 1, column 36, line 7, change "D-Thi-D-Pal(3)" to --D-Thi, D-Pal(3)--.

Claim 1, column 36, line 12, change "Ome" to --OMe--.

Claim 1, column 36, line 13, change "A D-Amino" to --a D-amino--.

Claim 1, column 36, line 23, before "optionally" insert --an--.

Claim 1, column 36, line 31, change "4, 5,6,7-" to --4,5,6,7- --.

Claim 2, column 36, line 47, change "Ome" to --OMe--.

Claim 2, column 36, line 52, after "are" insert --as--.

UNITED STATES PATENT AND TRADEMARK OFFICE
CERTIFICATE OF CORRECTION

PATENT NO. : 5,091,367
DATED : February 25, 1992
INVENTOR(S) : Wolfgang Konig, et al.

It is certified that error appears in the above-indentified patent and that said Letters Patent is hereby corrected as shown below:

Claim 3, column 36, line 63, before "D-amino" change "the" to --a--.

Signed and Sealed this

Nineteenth Day of October, 1993

*Attest:*

BRUCE LEHMAN

*Attesting Officer*  *Commissioner of Patents and Trademarks*